United States Patent [19]
Walt et al.

[11] Patent Number: 5,250,264
[45] Date of Patent: Oct. 5, 1993

[54] METHOD OF MAKING IMAGING FIBER OPTIC SENSORS TO CONCURRENTLY DETECT MULTIPLE ANALYTES OF INTEREST IN A FLUID SAMPLE

[75] Inventors: David R. Walt, Lexington; Steven M. Barnard, Medford, both of Mass.

[73] Assignee: Trustees of Tufts College, Medford, Mass.

[21] Appl. No.: 994,552

[22] Filed: Dec. 21, 1992

Related U.S. Application Data

[63] Continuation of Ser. No. 645,787, Jan. 25, 1991.

[51] Int. Cl.⁵ .................. G01N 21/00; A61B 5/00; G02B 6/24
[52] U.S. Cl. .................. 422/82.07; 385/12; 264/1.4; 264/1.5; 264/78; 422/82.06
[58] Field of Search .............. 422/68.1, 82.05, 82.06, 422/82.07, 82.08, 82.09, 82.11; 435/291, 808; 436/164, 172, 800. 805; 385/12; 250/227.23; 427/163, 492, 500; 156/273.3. 275.5, 275.7, 296; 8/647; 264/1.4, 1.5, 78

[56] References Cited

U.S. PATENT DOCUMENTS

| | | | |
|---|---|---|---|
| 4,523,092 | 6/1985 | Nelson | 250/227 |
| 4,582,809 | 4/1986 | Block et al. | 436/527 |
| 4,758,298 | 7/1988 | Goorsky et al. | 264/1.5 |
| 4,785,814 | 11/1988 | Kane | 128/634 |
| 4,822,746 | 4/1989 | Walt | 436/528 |
| 4,826,278 | 5/1989 | Gartside, III et al. | 264/1.5 |
| 4,842,783 | 6/1989 | Blayloch | 128/634 |
| 4,999,306 | 3/1991 | Yafuso et al. | 436/68 |
| 5,012,809 | 5/1991 | Shulze | 128/634 |
| 5,019,350 | 5/1991 | Rhum et al. | 422/82.07 |
| 5,047,627 | 9/1991 | Yimet et al. | 250/227.23 |
| 5,146,529 | 9/1992 | Mizutani | 385/103 |

FOREIGN PATENT DOCUMENTS 0336985 10/1989 European Pat. Off. ............ 128/634

Primary Examiner—Robert J. Warden
Assistant Examiner—T. A. Trembley
Attorney, Agent, or Firm—David Prashker

[57] ABSTRACT

The present invention provides a unique fiber optic sensor which is able to conduct multiple assays and analyses concurrently using a plurality of different dyes immobilized at individual spatial positions on the surface of the sensor. The present invention also provides apparatus for making precise optical determinations and measurements for multiple analytes of interest concurrently and provides methods of detection for multiple analytes of interest which can be correlated with specific parameters or other ligands for specific applications and purposes.

6 Claims, 18 Drawing Sheets

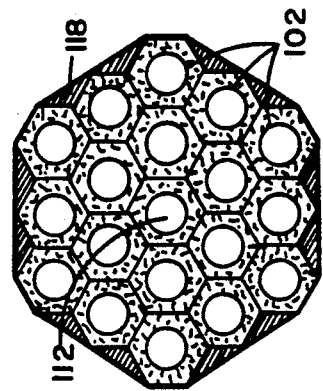
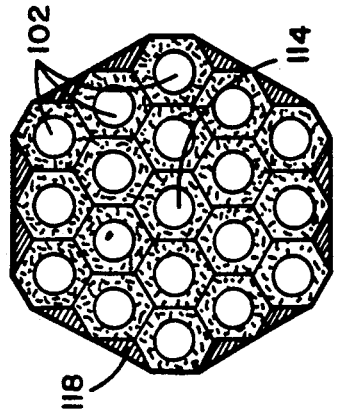
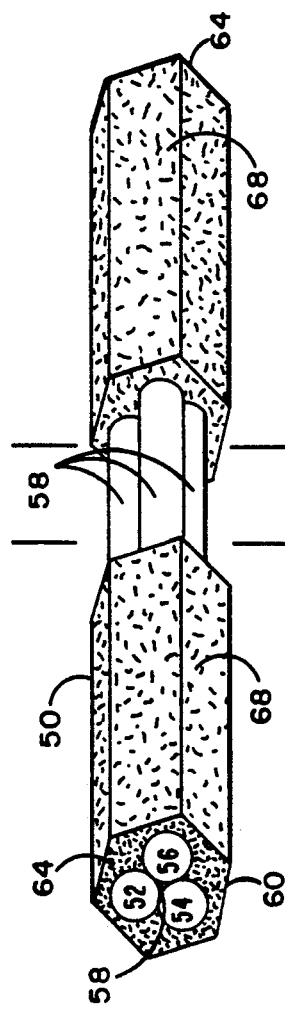
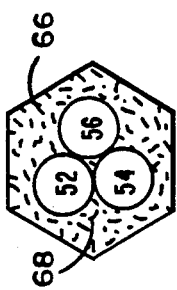
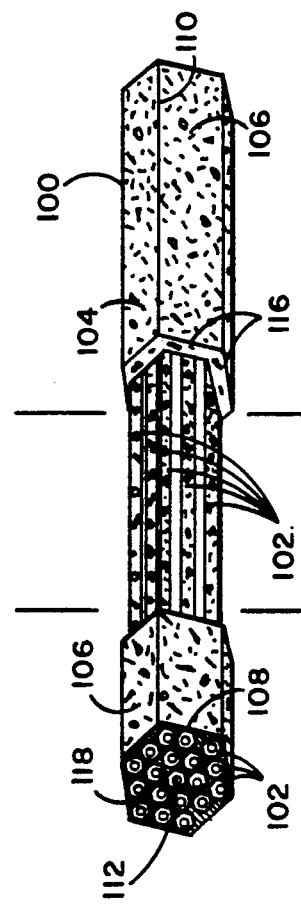

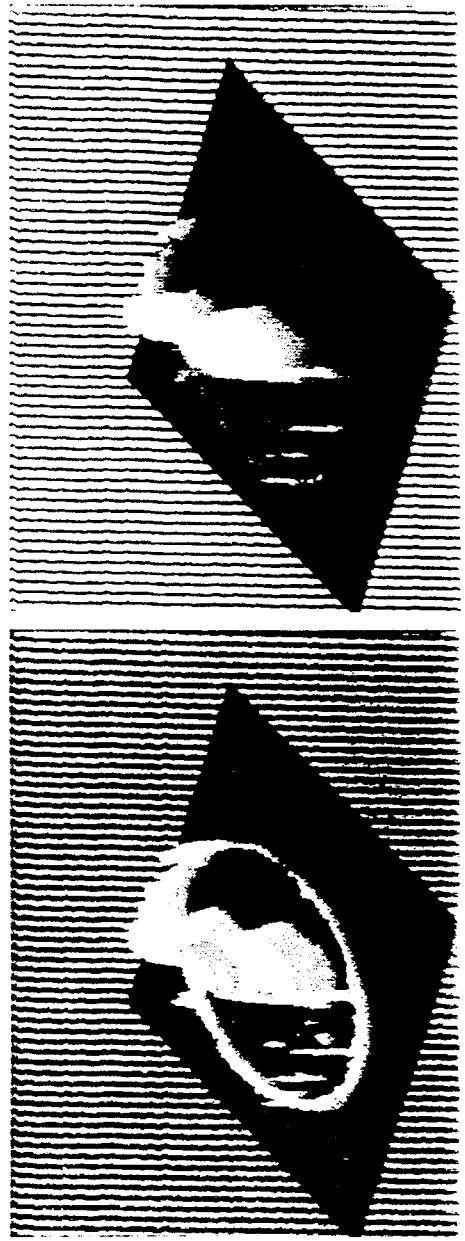

METHOD OF MAKING IMAGING FIBER OPTIC SENSORS TO CONCURRENTLY DETECT MULTIPLE ANALYTES OF INTEREST IN A FLUID SAMPLE

This is a continuation of application Ser. No. 645,787, filed on Jan. 25, 1991.

FIELD OF THE INVENTION

The present application is generally concerned with fiber optic sensors and light absorbing dyes which in combination are employed for qualitative and quantitative analytical determinations; and is specifically directed to the preparation and use of a single fiber optic array as a sensor for the detection of multiple analytes of interest concurrently.

BACKGROUND OF THE INVENTION

The use of optical fibers and optical fiber strands in combination with light energy absorbing dyes for medical, biochemical, and chemical analytical determinations has undergone rapid development, particularly within the last decade. The use of optical fibers for such purposes and techniques is described by Milanovich et al., "Novel Optical Fiber Techniques For Medical Application", Proceedings of the SPIE 28th Annual International Technical Symposium On Optics And Electro-Optics, Volume 494, 1980; Seitz, W. R., "Chemical Sensors Based On Immobilized Indicators And Fiber Optics" in *C.R.C. Critical Reviews In Analytical Chemistry*, Vol. 19, 1988, pp. 135-173; Wolfbeis, O. S., "Fiber optical Fluorosensors In Analytical Chemistry" in *Molecular Luminescence Spectroscopy, Methods and Applications* (S. G. Schulman, editor), Wiley & Sons, New York (1988); Angel, S. M., *Spectroscopy* 2(4):38 (1987); and Walt et al., "Chemical Sensors and Microinstrumentation", *ACS Symposium Series*, volume 403, 1989, p. 252. The optical fiber strands typically are glass or plastic extended rods having a small cross-sectional diameter. When light energy is projected into one end of the fiber strand (conventionally termed the "proximal end"), the angles at which the various light energy rays strike the surface are greater than the critical angle; and such rays are "piped" through the strand's length by successive internal reflections and eventually exit from the opposite end of the strand (conventionally termed the "distal end"). Typically bundles of these strands are used collectively as optical fibers in a variety of different applications.

For making an optical fiber into a sensor, one or more light energy absorbing dyes are attached to the distal end of the optical fiber. The sensor can then be used for both in-vitro and/or in-vivo applications. As used herein, light energy is photoenergy and is defined as electromagnetic radiation of any wavelength. Accordingly, the terms "light energy" and "photoenergy" include infrared, visible, and ultraviolet wavelengths conventionally employed in most optical instruments and apparatus; the term also includes the other spectral regions of X-ray and microwave wavelengths (although these are generally not used in conjunction with optical fibers).

Typically, light from an appropriate energy source is used to illuminate what is chosen to be the proximal end of an optical fiber or a fiber bundle. The light propagates along the length of the optical fiber; and a portion of this propagated light energy exits the distal end of the optical fiber and is absorbed by one or more light energy absorbing dyes. The light energy absorbing dye may or may not be immobilized; may or may not be directly attached to the optical fiber itself; may or may not be suspended in a fluid sample containing one or more analytes of interest to be detected; and may or may not be retainable for subsequent use in a second optical determination.

Once the light energy has been absorbed by the dye, some light energy of varying wavelength and intensity returns through the distal end of the optical fiber and is conveyed through either the same fiber or a collection fiber or fibers to a detection system where the emerging light energy is observed and measured. The interactions between the light energy conveyed by the optical fiber and the properties of the light absorbing dye—in the presence of a fluid sample containing one or more analytes of interest and in the absence of any analytes whatsoever— provide an optical basis for both qualitative and quantitative determinations. Merely illustrating the use of optical fiber sensors presently known in a variety of conditions, apparatus, dyes, and applications presently known are U.S. Pat. Nos. 4,822,746; 4,144,452; 4,495,293; and U.S. Pat. No. Re. 31,879. Moreover, in view of the microcircuitry and enhanced television technology presently available, a variety of light image processing and analytical systems have come into existence in order to both enhance, analyze and mathematically process the light energies introduced to and emerging from the absorbing dyes in such optical analytical techniques. Typically, these systems provide components for image capture; data acquisition; data processing and analysis; and visual presentation to the user. Commercially available systems include the QX-7 image processing and analysis system sold by Quantex, Inc. (Sunnydale, Calif.); and the IM Spectrofluoresence imaging system offered by SPEX Industries, Inc. (Edison, N.J.). Each of these systems may be combined with microscopes, cameras, and/or television monitors for automatic processing of all light energy determinations.

Of the many different classes of light absorbing dyes which conventionally are employed with bundles of fiber strands and optical fibers for different analytical purposes are those compositions which emit light energy after absorption termed "fluorophores" and those which absorb light energy and internally convert the absorbed light energy rather than emit it as light termed "chromophores." Fluorophores and fluorescent detection methods employing optical fibers are recognized as being markedly different and distinguishable from light energy absorbance and absorption spectroscopy.

Fluorescence is a physical phenomenon based upon the ability of some molecules to absorb light energy (photons) at specified wavelengths and then emit light energy of a longer wavelength and at a lower energy. Such emissions are called fluorescence if the emission is relatively long-lived, typically $10^{-11}$ to $10^{-7}$ seconds. Substances able to fluoresce share and display a number of common characteristics: the ability to absorb light energy at one wavelength or frequency; reach an excited energy state; and subsequently emit light at another light frequency and energy level. The absorption and fluorescence emission spectra are thus individual for each fluorophore; and are often graphically represented as two separate curves which are slightly overlapping. All fluorophores demonstrate the Stokes' shift—that is, the emitted light is always at a longer wavelength (and at a lower energy level) relative to the wavelength (and energy level) of the exciting light absorbed by the substance. Moreover, the same fluorescence emission spectrum is generally observed irrespective of the wavelength of the exciting light and, accordingly, the wavelength and energy of the exciting light may be varied within limits; but the light emitted by the fluorophore will always provide the same emission spectrum as emerging light. Finally, fluorescence may be measured as the quantum yield of light emitted. The fluorescence quantum yield is the ratio of the number of photons emitted in comparison to the number of photons initially absorbed by the fluorophore. For more detailed information regarding each of these characteristics the following references are recommended: Lakowicz, J. R., *Principles of Fluorescence Spectroscopy*, Plenum Press, New York, 1983; Freifelder, D., Physical Biochemistry, second edition, W. H. Freeman and Company, New York, 1982; "Molecular Luminescence Spectroscopy Methods and Applications: Part I" (S. G. Schulman, editor) in *Chemical Analysis*, vol. 77, Wiley & Sons. Inc., 1985; *The Theory of Luminescence*, Stepanov and Gribkovskii, Iliffe Books. Ltd., London, 1968.

In comparison, substances which absorb light energy and do not fluoresce usually convert the light energy into heat or kinetic energy. The ability to internally convert the absorbed light energy identifies the dye as a "chromophore." Dyes which absorb light energy as chromophores do so at individual wavelengths of energy and are characterized by a distinctive molar absorption coefficient at that wavelength. Chemical analyses employing fiber optic strands and absorption spectroscopy using visible and ultraviolet light wavelengths in combination with the absorption coefficient allow for the determination of concentration for specific analytes of interest by spectral measurement. The most common use of absorbance measurement via optical fibers is to determine concentration which is calculated in accordance with Beers' law; accordingly, at a single absorbance wavelength, the greater the quantity of the composition which absorbs light energy at a given photo wavelength, the greater the optical density for the sample. In this way, the total quantity of light absorbed directly correlates with the quantity of the composition in the sample.

Many of the recent improvements employing optical fiber sensors in both qualitative and quantitative analytical determinations concern the desirability of depositing and/or immobilizing various light absorbing dyes at the distal end of the optical fiber using a given technique or apparatus. In this manner, a variety of different optical fiber chemical sensors and methods have been reported for specific analytical determinations and applications such as pH measurement, oxygen detection, and carbon dioxide analyses. These developments are exemplified by the following publications: Freeman et al., *Anal. Chem*, 53:98 (1983); Lippitsch et al., *Anal. Chem. Acta*, 205:1, (1988); Wolfbeis et al., *Anal. Chem*. 60:2028 (1988); Jordan et al., *Anal. Chem*. 59:437 (1987); Cubbers et al., *Sens. Actuators* 1983; Munkholm et al., *Talanta* 35:109 (1988); Munkholm et al., *Anal. Chem*. 58:1427 (1986); Seitz, W. R., *Anal. Chem*. 56:16A-34A (1984); Peterson et al., *Anal. Chem*. 52:864 (1980); Saari et al., *Anal. Chem*. 54:821 (1982); Saari et al., *Anal. Chem*. 55:667 (1983); Zhujun et al., *Anal. Chem. Acta*. 160:47 (1984); and Schwab et al., *Anal. Chem*. 56:2199 (1984).

Despite these many innovations and developments, and without regard to whether the application is intended for in-vitro or in-vivo use, it was previously and remains today nearly impossible to measure multiple parameters and detect multiple analytes of interest in a fluid sample using a single optical fiber sensor. The axiomatic rule almost universally accepted is: one dye allows but one optical determination. Presently, therefore, a single fiber optical sensor uses a single dye reagent and can measure but one individual chemical analyte or species in a fluid sample. If more than one analytical determination is required, the use of several different fiber optical sensors each having a different single dye reagent are needed.

It is most important to recognize and to understand the reasons and basis for the axiomatic rule's existence and general acceptance. The useful spectral range for optical fibers is approximately 300-700 nm, a range due principally to higher attenuation outside this wavelength region. Most dyes have relatively broad excitation (absorption) and/or emission spectra. Consequently, when two or more dyes are combined (each dye being sensitive to a different analyte), there is typically significant overlap in their spectra; and this spectral overlap results in difficult-to-deconvolute signals arising from the returning (emerging) light from each dye. It is important to note that the optical fibers conventionally used for fiber optic sensors randomly mix all the light energy returning (emerging) from the distal end of the sensor. Thus, even if the dyes were positioned differently on the distal end of the sensor, the returning signals (emerging light energy) would still become randomly scrambled and therefore be rendered useless for making optical determinations. Only a very few sensor systems have been developed in which the sensor utilizes a plurality of dyes with minimal spectral overlap. Thus for general use purposes, the axiomatic rule has evolved that one dye permits but one optical determination.

Given the very few exceptions to the axiomatic rule, all conventional optical fiber sensors and systems now available demand the presence of a separate sensing optical fiber and dye reagent for each parameter or analyte to be measured. Each sensing fiber increases the size and complexity of the overall system; and geometrically increases the complexity and difficulty of making multiple optical determinations concurrently. Accordingly, the development of a single imaging fiber optic sensor able to utilize multiple dye reagents and to provide multiple optical determinations of different analytes of interest concurrently would be recognized as a major advance and substantial improvement by persons ordinarily skilled in this art.

SUMMARY OF THE INVENTION

The present invention is definable in alternative formats. A first definition provides a fiber optic sensor useful in an apparatus for concurrently detecting multiple analytes of interest in a fluid sample, the detection of each analyte of interest being correlatable with an individual optical determination. This fiber optic sensor comprises:

a plurality of individually clad, fiber optical strands disposed coaxially along their lengths and forming a unitary imaging fiber optic array having two discrete ends, said imaging fiber optical array being of determinable configuration and dimensions, said two ends of said imaging fiber optic array presenting two discrete optic array surfaces for precise spatial positional introduction and conveyance of light energy via different fiber optical strands within said imaging fiber optic array; and at least one light energy absorbing dye disposed individually at different spatial positions upon one of said optic array surfaces of said imaging fiber optic sensor, the individual spatial positioning of each dye upon said optic array surface serving to identify and distinguish each said dye from all other light energy absorbing dyes disposed on said optic array surface, each of said individual spatially positioned dyes reacting specifically with one analyte of interest;

A second, alternative definition of the present invention is a method for making a fiber optical sensor able to concurrently detect multiple analytes of interest in a fluid sample, the detection of each analyte of interest being correlatable with an individual optical determination, said method comprising the steps of:

obtaining an imaging fiber optic array comprising a plurality of individually clad, fiber optical strands disposed coaxially along their lengths and forming a unitary fiber optic array having two discrete ends, said imaging fiber optical array being of determinable configuration and dimensions, said two ends of said imaging fiber optic array presenting two discrete optic array surfaces for precise spatial positional introduction and conveyance of light energy via said fiber optical strands;

preparing a first photopolymerizable dye mixture comprising a first light energy absorbing dye and a monomer mixture polymerizable by light energy;

preparing a second photopolymerizable dye mixture comprising a second light energy absorbing dye and a monomer mixture polymerizable by light energy;

placing one of said optic array surfaces of said imaging fiber optic array into contact with said first photopolymerizable dye mixture;

introducing light energy to a first portion of the other optic array surface of said imaging fiber optic array such that a first group of fiber optical strands within said imaging fiber optic array conveys said introduced light energy to a first spatial position on said contacted optic array surface and causes said first dye mixture to photopolymerize at said first spatial position on said contacted optic array surface as an immobilized first dye, said spatially positioned first dye reacting specifically with one analyte of interest in a fluid sample;

placing said contacted optic array surface of said imaging fiber optic array into additional contact with said second photopolymerizable dye mixture; and introducing light energy of a second wavelength to a second portion of said other optic array surface such that a second group of fiber optical strands within said imaging fiber optic array conveys said introduced light to a second spatial position on said contacted optic array surface and causes said second dye mixture to photopolymerize at said second spatial position on said contacted optic array surface as an immobilized second dye, said spatially positioned second dye reacting specifically with one analyte of interest in a fluid sample.

A third, alternative definition of the present invention is an apparatus for concurrently detecting multiple analytes of interest in a fluid sample, the detection of each analyte of interest being correlatable with an individual optical determination. This apparatus comprises:

a fiber optic sensor comprising a plurality of individually clad, fiber optical strands disposed coaxially along their lengths and forming a unitary imaging fiber optic array having two discrete ends, said imaging fiber optical array being of determinable configuration and dimensions, said two ends of said imaging fiber optic array presenting two discrete optic array surfaces for precise spatial positional introduction and conveyance of light energy via different fiber optical strands within said imaging fiber optic array, and at least one light energy absorbing dye disposed individually at different spatial positions upon one of said optic array surfaces of said imaging fiber optic array, the individual spatial positioning of each dye upon said optic array surface serving to identify and distinguish each said dye from all other light energy absorbing dyes disposed on said optic array surface, each of said individual spatially positioned dyes reacting specifically with one analyte of interest;

means for placing said spatially positioned dyes on said optical array surface of said fiber optic sensor in reactive contact with a fluid sample;

means for concurrently introducing light energy of determinable wavelength to portions of an optic array surface of said fiber optic sensor such that fiber optical strands of said fiber optic sensor convey said introduced light energy concurrently and individually illuminate each of said spatially positioned dyes on said optic array surface concurrently; and means for concurrently detecting emerging light energy from each of said concurrently and individually illuminated, spatially positioned dyes disposed upon said optic array surface, said detected emerging light energy from each spatially positioned dye serving as an optical determination for one analyte of interest believed present in the fluid sample.

A fourth, alternative definition of the present invention provides a method for concurrently detecting multiple analytes of interest in a fluid sample, the detection of each analyte of interest being correlatable with an individual optical determination. This method comprises the steps of:

obtaining a fiber optic sensor comprising a plurality of individually clad, fiber optical strands disposed coaxially along their lengths and forming a unitary imaging fiber optic array having two discrete ends, said imaging fiber optical array being of determinable configuration and dimensions, said two ends of said imaging fiber optic array presenting two discrete optic array surfaces for precise spatial positional introduction and conveyance of light energy via different fiber optical strands within said imaging fiber optic array, and at least one light energy absorbing dye disposed individually at different spatial positions upon one of said optic array surfaces of said imaging fiber optic array, the individual spatial positioning of each dye upon said optic array surface serving to identify and distinguish each said dye from all other light energy absorbing dyes disposed on said optic array surface, each of said individual spatially positioned dyes reacting specifically with one analyte of interest;

placing said spatially positioned dyes on said optic array surface of said fiber optic sensor in reactive contact with a fluid sample;

concurrently introducing light energy of determinable wavelengths to portions of said other optic array surface of said fiber optic sensor such that fiber optical strands of said fiber optic sensor convey said introduced light energy concurrently and individually illuminate each of said spatially positioned dyes on said proximal optic array surface concurrently; and concurrently detecting emerging light energy from each of said concurrently and individually illuminated, spatially positioned dyes disposed upon said optic array surface, said detected emerging light energy from each spatially positioned dye serving as an optical determination for one analyte of interest believed present in the fluid sample.

BRIEF DESCRIPTION OF THE FIGURES

The present invention may be more easily and completely understood when taken in conjunction with the accompanying drawing, in which:

FIG. 4 is an overhead view of another embodiment for an individually clad, fiber optical strand;

FIGS. 5A and 5B are views of the two optical end surfaces of the optical fiber strand shown in FIG. 4;

FIG. 6 is an overhead view of an imaging fiber optic array constructed using the fiber optical strand of FIG. 1;

FIGS. 7A and 7B are views of the proximal and distal optic array surfaces of the imaging fiber optical array shown in FIG. 6;

FIGS. 20A and 20B are imaging photographs of contour plots of light intensity for the dyes on one optic surface of the fiber optic sensor using the apparatus of FIG. 18;

DETAILED DESCRIPTION OF THE INVENTION

Figure 1:
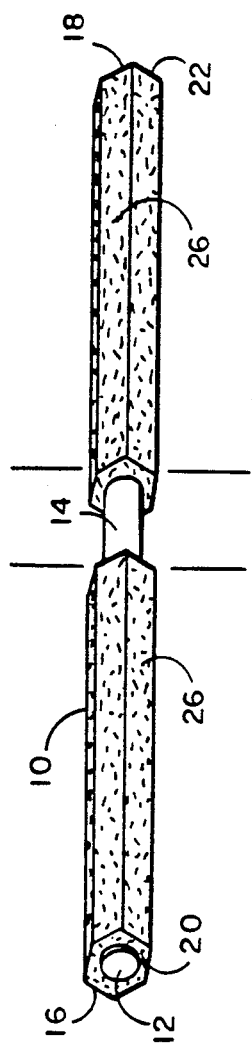
FIG. 1 is an overhead view of a preferred individually clad, fiber optical strand.

The present invention is a marked improvement in fiber optic sensors; apparatus, systems and assemblies; and methods for performing qualitative and quantitative optical measurements using a unique fiber optic sensor. The physical construction of this singular fiber optic sensor and the manner of its making are the critical and demanding aspects of the invention. The apparatus, methods for making determinations, and systems of qualitative and quantitative detection subsequently described are based and rely upon the existence and use of the unique fiber optic sensor as an essential component.

Although the unique fiber optic sensor and the other aspects of the present invention may bear a superficial similarity to conventionally known optical fibers, fiber optic strands, and fluorometric and colorimetric optical systems for making analytical determinations, it will be recognized and appreciated that the present invention provides multiple benefits and major advantages not previously available heretofore. These include:

1. A fully constructed fiber optical sensor comprising individually clad, fiber optical strands disposed coaxially along their lengths to form a discrete imaging fiber optic array which has one or more light energy absorbing dyes disposed individually at different spatial positions upon an end surface of the optic array. This unique fiber optic sensor permits the use of one or more dyes to measure a variety of different parameters such as pH, oxygen, carbon dioxide and the like using but a single discrete sensor. The use of multiple dyes in combination with a single, discrete imaging fiber optic array, insofar as is presently known, has never before been constructed for any purpose or application.

2. A variety of different in-vitro measurements and analytical determinations may now be made using a single fiber optic sensor prepared in accordance with the present invention. The in-vitro applications and assay techniques may be performed concurrently using one or multiple fluid samples. Each concurrently conducted measurement or determination for different analytes of interest is made individually, accurately, and precisely. The observed empirical results are then correlated and/or computed individually to provide precise information regarding a variety of different parameters or ligands is individually.

3. The unique fiber optic sensor as well as the apparatus and measurement procedures described hereinafter may be employed in a variety of different in-vivo conditions with both humans and animals. The present invention provides accurate and precise measurements and determinations using a single discrete fiber optic sensor rather than the conventional bundle of different sensors joined together for limited purposes. The present invention thus provides a minimum-sized diameter sensor for in-vivo catherization; a minimum intrusion into the bloodstream or tissues of the living subject for assay purposes; and a minimum of discomfort and pain to the living subject coupled with a maximum of accuracy and precision as well as multiplicity of parameter measurement in both qualitative and/or quantitative terms.

4. The present invention provides a fiber optic sensor suitable for use with multiple light systems and apparatus; and is particularly suitable for use with two or more light energy absorbing dye compositions having overlapping spectral properties. Unlike conventionally known fiber optic systems which are typically limited to certain light energy ranges or wavelengths exclusively, the present invention may be prepared and employed with any measurable range of light energy or wavelength which can be conveyed or propagated through a fiber optic strand including infrared light, visible light and ultraviolet light wavelengths. The diversity and range of the sensor is limited only by the wavelengths of light energy required and the choice of light energy absorbing dye(s) available from the entirety of those conventionally known today.

5. The fiber optic sensors of the present invention permit the use of a single light-absorbing dye for making different optical determinations and measuring multiple parameters concurrently. Clearly via the requirement of at least two individual spatial positions for the dye on the optic array end surface, a spatial resolution of the forthcoming individual light energy intensities and wavelengths is created; and an effective separation of individual light signals and concomitant avoidance of photon intermixing is maintained. There is therefore no overlap of spectral properties and characteristics between the different spatial locations despite the use of a single dye; and no need for spectral resolution of the different light energy signals because of the spatial resolution effects caused by the individual spatial positionings for the single dye.

6. The present invention optionally permits the user to employ the unique fiber optic sensor in a fully automated, monitored, and even computerized system. A number of alternative apparatus formats are possible and suitable. The goal of all these automated systems is to provide the user with an apparatus that can display light intensity and location nearly simultaneously. Typically, they are of two general types: phototubes and charge coupled devices (or "CCD's"). A conventionally constructed camera is but one example of such automated apparatus; and in an extreme case, even the detection elements in the camera could be used alone.

In one desirable apparatus format, the unique optic fiber sensor is employed with a microscope objective, a camera, a visual monitor, and a computerized image processing and analytical program. In this embodiment providing a fully automated, computer controlled, processing apparatus and measurement system, the intensity and wavelength of light energy is carefully controlled; the light energy is introduced to the appropriate portions of the fiber optic sensor at specifically controlled occasions and durations; and the resulting optic images and emerging light photons conveyed for analytical measurement are mathematically processed and correlated via computer programs into immediately useful data and often visualized on a television monitor or other display apparatus. By using such fully automated, computerized apparatus and analytical systems, not only are a variety of different optical determinations made and diverse parameters measured concurrently within a single fluid sample; but also many different fluid samples may be analyzed individually seriatim for detection of multiple analytes of interest concurrently—each individual fluid sample following its predecessor in series.

7. The singular fiber optic sensor of the present invention allows the user to conduct both chemical analyses and optical imaging by employing but one construction and system. The sensor, being comprised of fiber optical strands, permits direct imaging and viewing of the environment in which the sensor is placed. The analytic determinations involving the immobilized dyes of the sensor and the assessment of various parameters may also be performed at will as the needs or desires of the user requires. The dual capability of imaging and chemical analysis using a single sensor is particularly advantageous for in-vivo applications such as angioplasty where it would be most desirable to see where the optical fiber lies within the patient; use the fiber to deliver the therapeutic treatment (such as a laser light treatment); as well as to concurrently measure the efficacy of the treatment (such as cholesterol or calcium ion values immediately after laser light treatment).

Since the present invention is definable in multiple formats and may be employed in different modes for a variety of divergent purposes and applications, the subject matter as a whole which is the present invention will be presented and described individually as component parts and then collectively as assemblies in order that the prospective user may more quickly recognize and appreciate their major differences and distinctions in comparison to the fiber optic apparatus and systems conventionally known.

I. The Organization and Construction of the Singular Fiber Optic Sensor

The unique fiber optic sensor comprises two essential components: a plurality of individually clad fiber optical strands disposed coaxially along their lengths to form a discrete imaging fiber optic array; and one or more light energy absorbing dyes disposed individually at different spatial positions upon a surface of the imaging fiber optic array. Each component will be described in detail.

A. The Imaging Fiber Optic Array

The unique imaging fiber optic array, its organization and construction, and its component parts are illustrated by FIGS. 1-8 respectively. Each discrete, imaging fiber optic array is comprised of a plurality of individually clad, fiber optical strands disposed coaxially along their lengths to form a single, discrete, construction. The smallest common repeating unit within the optical unit is thus a single fiber optical strand. The manner in which these optical strands are prepared and the manner in which these prepared optical strands are joined collectively into an organized optical array are fundamental to a proper understanding and use of the present invention.

The individually clad, fiber optical strand

Figure 2A:
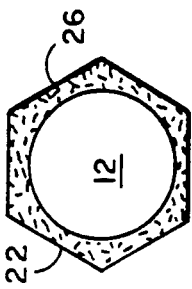
FIGS. 2A and 2B are views of the proximal and distal surfaces of the fiber optical strand shown in FIG. 1.
Figure 2B:
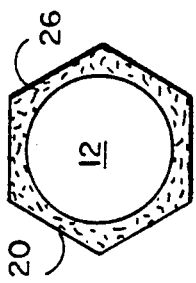

A preferred fiber optical strand is illustrated by FIGS. 1 and 2A and 2B. As seen therein, an individual fiber optical strand 10 is comprised of a single optical fiber 12 having a rod-like shaft 14 and two fiber ends 16, 18, each of which provides a substantially planar end surface. The intended distal surface 20 at the fiber end 16 is illustrated by FIG. 2A while the intended proximal surface 22 at the fiber end 18 is illustrated within FIG. 2B. It will be recognized and appreciated that the terms is "proximal" and "distal" are relative and interchangeable until the strand is ultimately positioned in an apparatus. The optical fiber 12 is composed typically of glass or plastic and is a flexible rod able to convey light energy introduced at either of its ends 16, 18. Such optical fibers 12 are conventionally known and commercially available. Alternatively, the user may himself prepare optical fibers in accordance with the conventional practices and techniques reported by the scientific and industrial literature. Accordingly, the optical fiber 12 is deemed to be conventionally known and available as such.

It will be appreciated that FIGS. 1-2 are illustrations in which the features have been purposely magnified and exaggerated beyond their normal scale in order to provide both clarity and visualization of extreme detail. Typically, the conventional optical fiber has a cross section diameter of 5-500 micrometers and is routinely employed in lengths ranging between centimeters (in the laboratory) to kilometers (in field telecommunications). Moreover, although the optical fiber 12 is illustrated via FIGS. 1-2 as a cylindrical extended rod having substantially circular proximal and distal end surfaces, there is no requirement or demand that this specific configuration be maintained. To the contrary, the optical fiber may be polygonal or asymmetrically shaped along its length; provide special patterns and shapes at the proximal and/or distal faces; and need not present an end surface which is substantially planar. Nevertheless, for best efforts, it is presently believed that the substantially cylindrical rod-like optical fiber having planar end surfaces is most desirable.

Each optical fiber 12 is desirably, but not necessarily, individually clad by cladding 26 axially along its length. This cladding 26 is composed of any material which has a lower refractive index and prevents the transmission of light energy photons from the optical fiber 12 to the external environment. The cladding material 26 may thus be composed of a variety of radically different chemical formulations including various glasses, silicones, plastics, cloths, platings, and shielding matter of diverse chemical composition and formulation. The manner in which the optical fiber 12 is clad is also inconsequential and of no importance to the present invention. Those methods of deposition, extrusion, painting, and covering are scientifically and industrially available; and any of these known processes may be chosen to meet the requirements and convenience of the user. Moreover, the quantity of cladding employed need be only that minimal amount which effectively prevents light energy conveyed by the optical fiber 12 from escaping into the general surroundings. It will be recognized and appreciated therefore, that the depth of cladding 26 as appears within FIGS. 1 and 2 respectively is greatly exaggerated and purposely thickened in order to show the general relationship; and is without scale or precise ratio between the cladding 26 and the optical fiber 12.

It will also be recognized that the configuration of the cladding 26 as appears within FIGS. 1 and 2 has been shaped as a six-sided coating as a preferred embodiment only. For reasons as will become clear subsequently, it is desirable that the cladding 26 take form as a multi-sided and regular geometric form rather than as a round, oval, circular or irregular shape. The illustrated configuration, however, is merely a preferred embodiment of the cladding 26 as it extends coaxially along the length of the optical fiber 12. For purposes of added clarity also, FIG. 1 reveals the individually clad, optical fiber strand 10 in partial cross-section to demonstrate the relationship between the optical fiber 12 and the cladding 26 which is coextensive along its length.

Figure 3A:
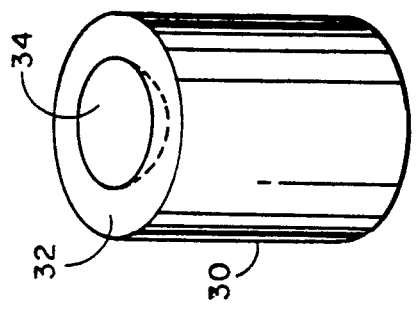
FIGS. 3A and 3B are alternative constructions of the optical end surface for the fiber optical strand shown in FIG. 1.
Figure 3B:
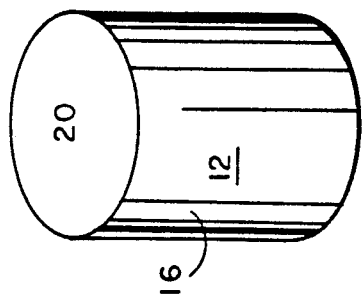

The user also has a variety of choices at his discretion regarding the configuration of the distal end 16 of the optical fiber 12 as is demonstrated by FIG. 3A and 3B. As seen via FIG. 3A, the distal end 16 is substantially cylindrical in shape and desirably presents a surface 20 which is substantially planar and smooth. As an alternative in FIG. 3B, the distal end 30, while maintaining its substantially cylindrical shape, nevertheless provides a very different end surface for the optical fiber 12. The surface 32 includes a depression or well 34 which extends into the substance of the optical fiber 12 at a depth typically of several micrometers. Although the well 34 appears substantially circular within FIG. 3B, oval or irregularly configured depressions may also be employed as fits the needs or convenience of the user. Similarly, the void volume of the well 34 from its greatest depth to the surface 32 may also be considerably varied.

It will be recognized and appreciated as well that the range and variety of dimensional and configurational divergence for the strand end is limited only by the user's ability to subsequently dispose and immobilize a dye composition/formulation on the intended distal surface of the optical fiber 12. The alternative illustrated by FIG. 3B will increase the quantity of dye materials deposited and also permit a greater surface area of dye for reactive contact on the surface for specific uses and assay applications. In some embodiments, the greatest possible surface, area configurations of the distal end surface may be highly desirable as an aid; nevertheless, for most general assay purposes, both quantitative and qualitative, the intended distal surface illustrated within FIG. 3A as a substantially planar and smooth surface is deemed to be suitable and desirable.

Another alternative embodiment of an individually clad, fiber optical strand suitable for use in forming an imaging fiber optic array is illustrated by FIGS. 4, 5A, and 5B. This alternative embodiment of the individually clad, fiber optical strand 50 employs not one, but a plurality of optical fibers 52, 54, 56 which are disposed coaxially along their lengths as a grouping 58. The grouping 58 appears within FIGS. 4, 5A, 5B as a trio of optical fibers, but may include any number of optical fibers greater than one. The trio grouping 58 provides an intended distal group end 60 and a distal end surface 64 as well as an intended proximal group end 62 and a proximal end surface 66. The end surfaces 64, 66 are illustrated as substantially planar and smooth circular surfaces joined together as a group but in fact may have any configuration and surface including those individually illustrated within FIG. 3 previously herein.

The trio grouping 58 of optical fibers is clad along the entirety of its length with cladding material 68 which has been configured in hexagonal shape. Here also, the cladding material 68 is purposely exaggerated and greatly thickened with respect to the trio grouping 58 to illustrate the relationship between them. As before, the cladding material 68 may be comprised of any matter which will adhere indefinitely to the optical fibers 52, 54, 56 indefinitely and provide a sheath having refractive index less than the strand core to allow for internal reflection. The sheath thus prevents loss of light energy photons conveyed by one trio grouping 58 into another grouping or into the general environment. The cladding may thus be composed of any material and configured in any shape of any thickness and in any dimensions so long as a fiber optical strand 50 is constructed. Note also that FIG. 4 appears in partial cross-sectional view to demonstrate the relationship of the cladding material 68 to the trio grouping of optical fibers 58 without regard to particular scale or ratio of thicknesses.

For general construction of the optic fiber sensor and for most purposes and applications of the improved optical detecting system and procedures described hereinafter, it is desirable to employ the individually clad, fiber optical strand illustrated by FIGS. 1, 2A, 2B in preference to that embodiment illustrated within FIGS. 4, 5A, 5B. Clearly, the optical fiber strand 10 of FIG. 1 comprising a single optical fiber is unable to transmit light energy photons to any other optical fiber or strand. Accordingly, the potential for photon loss, distortion, or other optical error is minimized and reduced. In comparison, the trio grouping 58 of optical fibers illustrated within the individually, clad optical fiber strand 50 of FIG. 4 allows the light energy photons conveyed by each optical fiber 52, 54, 56 individually to migrate partially from one fiber to either or both of the other adjacently positioned fibers. This "cross-talk" phenomenon provides an undesirable risk of increasing the potential for quantum loss of light energy photons; for allowing alteration of light energy via the cross migrations of photons; and for permitting a greater range of reflection angles for distortion or loss of the light energy as it travels axially along the length of the trio grouping. For these reasons, the single optical fiber mode of construction is preferable to the use of multioptical fiber groupings—although each embodiment is clad—in order to achieve greater precision and accuracy.

The organizational array

While the single, repeating unit, component of the fiber optic sensor is the individually clad, fiber optic strand described previously, it is the organizational positioning and alignment of many individually clad, fiber optical strands into a unitary article which is the essence of the imaging fiber optic array. A typical imaging fiber optic array is illustrated by FIGS. 6, 7, and 8 respectively in which the unitary imaging fiber optical array 100 appears in exaggerated, highly simplified views without regard to scale. A plurality of individually clad, fiber optical strands 102 lie disposed coaxially along their respective lengths and form a discrete, unitary optic array 104 of determinable configuration and dimensions. The optic array 104 comprises a unitary, rod-like collective body 106 having intended distal and proximal collective ends 108, 110. The intended distal collective end 108 provides a substantially planar and smooth optic array surface 112; similarly, the intended proximal collective end 110 provides an optic array surface 114. The topographical surface 116 is the result of the cladding of each fiber optical strand 102 collectively with such additional coating material 118 such that the individually clad, fiber optical strands 102 remain together collectively as a discrete and unitary whole; and that the exterior surface 116 of the collective array body 106 be configured and dimensioned in an assembly acceptable and useful manner. It will be recognized and appreciated that a hexagonal configuration and topography is maintained and presented by the unitary imaging fiber optic array 100 as a preferred embodiment. Nevertheless, any other regular or irregular configuration and design may be achieved to satisfy the individual user's needs or desires.

For purposes of clarity and ease of understanding, FIGS. 7 and 8 present a very limited and greatly reduced number of individually clad, fiber optical strands 102 as forming the optical array 104. A total of only nineteen individually clad, fiber optical strands are seen to comprise the optical array 104 in FIGS. 7 and 8 in greatly magnified and scale-exaggerated views. Moreover, the relationship of the optical array surface 112 with respect to the other optical array surface 114 becomes simplified and more readily appreciated when using this limited number of nineteen clad fiber optic strands. In practice and reality, however, it is estimated that there typically are 1000–3000 fiber optical strands in a conventional imaging fiber of 0.5 mm diameter; and nearly 1 million strands per square millimeter. Thus the true total number of individually clad, fiber optic strands forming the unitary imaging fiber optic array will be almost as great, the total number varying with the cross-sectional diameter of each optical fiber and the thickness of the cladding material employed when constructing the optical fiber strands themselves.

Figure 8A:
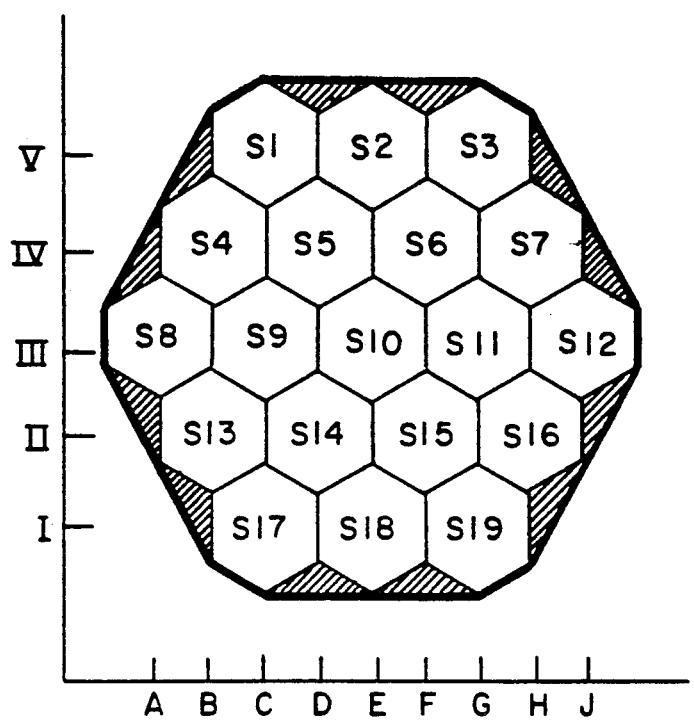
FIGS. 8A and 8B are numerical coordinated views of the two optic array surfaces of FIGS. 7A and 7B to identify precise spatial positions.
Figure 8B:
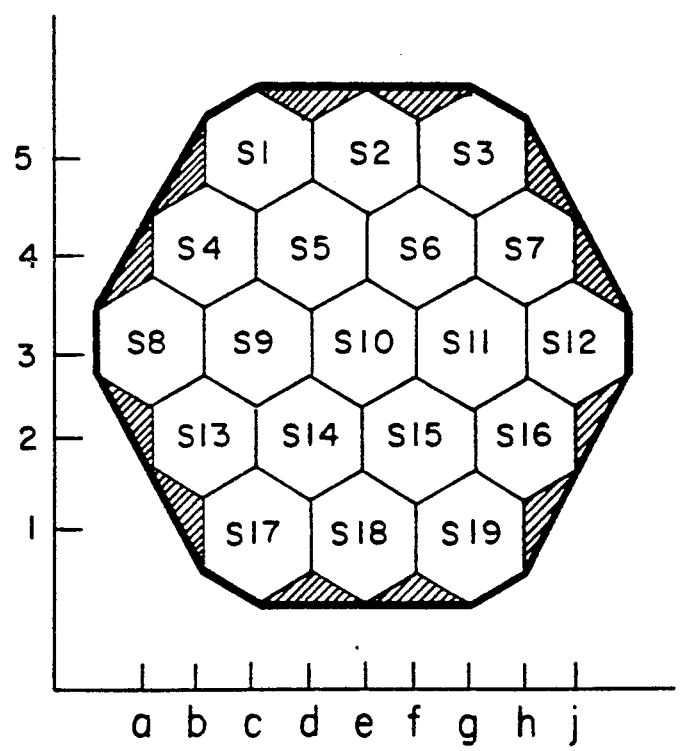

The construction organization and positional alignment within a typical imaging fiber optical array is revealed by FIG. 6 in which a partial cross-sectional view is presented by FIGS. 8A and 8B respectively. For descriptive purposes only, each of the nineteen, individually clad, optical fiber strands 102 has been arbitrarily assigned an identifying number S1–S19 as shown via FIG. 8. The intended distal optic array surface 112 appears in FIG. 8A and shows that each of the individual fiber optical strands S1–S19 can be identified and distinguished from its adjacently disposed neighbor as well as from any other fiber optical strand 102 within the unitary array 104 by a set of spatial positioning coordinate numbers. The optic array surface 112 may be divided linearly into two axis directions as is illustrated by FIG. 8A. The exact location of the S1 strand is thus identifiable by the numerical coordinates "VC". Similarly, the exact spatial positioning of the S15 fiber is designatable as "IIF". In this manner, the individual spatial position of each optical fiber strand S1–S19 is thus completely locatable and identifiable using the coordinate numeral labelling system.

The other optic array surface 114 allows for a similar mode of identification by linear spatial positioning of each individual optical fiber strand—again as a result of dual-axis numerical coordinates. Accordingly, fiber S1 is located precisely at numerical position "5c", and fiber S15 is identifiable, locatable, and distinguishable from all other fibers at the optic array surface by its individual numerical coordinates "2f". In this manner, the precise and exact position of each individually clad fiber optical strand 102 on each of the 17 discrete optic array surfaces 112, 114 can be located, identified, and specified via a series of two different numerical coordinates. The intended proximal and distal optic array surfaces are thus completely identifiable and distinguishable as per individual fiber optical strand 102 despite its incorporation collectively into the collective body 106 of the unitary imaging fiber optical array 100.

It will be recognized and appreciated also that the overall organization of the individually clad, fiber optical strands 102 within the unitary array 100 is as aligned, parallel strands which maintain its relative organizational positioning in a consistent manner over the entirety of the collective body 106. This is deemed to be the most desirable and most easily constructable organizational scheme and presentation for making the optical fiber sensor comprising the present invention. Although this highly organized and rigidly aligned collective construction is deemed to be most desirable, this high degree of organization is not an absolute requirement for each and every embodiment of the unitary optical array. Alternative manufacturing practices allow for a random disposition of individually clad, optical fiber strands to be disposed coaxially along their lengths to form a unitary imaging fiber optical array having two optic array surfaces. Although less desirable, a random disposition and random alignment of individually clad, optical fiber strands will also result in a collective body of optical fibers and in proximal and distal collective ends which provide two discrete optic array surfaces. In such embodiments, however, an optical fiber strand 102 whose intended distal end would be found to be at numerical position "VJ" could very randomly present an intended proximal end position designated as "1c". It will be recognized therefore that while the individually clad, optical fiber strands are disposed adjacent one another along the entirety of their lengths, their disposition lies in a random organizational construction. There is no requirement that the positioning of the intended proximal end of the strand be aligned and identical with the positioning of the intended distal end within the unitary optic array. In such randomly organized optical array constructions, therefore, the precise proximal and distal end positioning for the fiber strands would be measured and identified merely by passing light energy through individual optical fibers at one optic array end and empirically determining the location of the light energy photons exiting from the other of the same individual fiber strand. Although far more laborious and inconvenient, by following this extra step of empirically coordinating the proximal and distal ends of each individual optical fiber strand in the unitary array, an analogous exact set of numerical coordinates identifying the precise spatial positioning of the fiber at each end of the array may be obtained.

The entirety of the construction for the unitary imaging optical fiber array (whether completely uniformly aligned, semi-aligned, or randomly organized) provides a means of introducing light energy photons of any determinable wavelength at one position on one optic array surface and then allows one to predict accurately the spatial position of the exiting light energy at the other optic array surface. Therefore, by using the preferred highly organized and rigidly maintained parallel alignment illustrated within FIGS. 8A and 8B as the intended proximal and distal optic array surfaces respectively of a unitary imaging fiber optic array, the user may introduce light energy to a specific spatial location on the optic array surface 114 for example, only to fibers S1, S4 and S5—and have accurate knowledge and confidence that the light energy would be conveyed only by those three optical fiber strands and exit from numerical positions VC, IVB, and IVD alone. No other light energy would appear from any other spatial position from the optic array surface 112. Similarly, were light energy of specific wavelengths introduced at the optic array surface 112 via fibers S13, S14, and S17 respectively, the user would be able to accurately predict and identify that the light energy will be conveyed by only these three optical fibers; and would exit only at the optic array surface 114 at numerical coordinate position numbers 2b, 2d and 1c respectively and from no other spatial positions on this optic array surface. In this manner, not only the individual spatial positioning of each individually clad optical fiber strand but also the identification and precise location of light energy photons emerging from specifically positioned optical fiber strands from within specific portions of a single array surface now becomes practical and employable.

Accordingly, the critical and essential requirements of any unitary imaging optical fiber array constructed in accordance present invention allows and demands the capability for precise spatial positional introduction and conveyance of light energy via different fiber optical strands within the collective body of the imaging fiber optical array. This capability to introduce light energy photons at precise spatial positions at one optic array surface of a unitary array; to convey the introduced light energy along the length of only a few fiber optical strands; and to culminate with the exit of the conveyed light energy at a second, precisely known, spatial position on the other optic array surface of the unitary array is the hallmark and essence of the singular fiber optic sensor presented herein.

B. Light Energy Absorbing Dyes, Dye-Generating Substances, and Dye Mixtures

The unique fiber optical sensor of the present invention requires that one or more light energy absorbing dyes and/or dye-generating substances and/or dye mixtures be disposed individually at different spatial positions upon the optical array surface at one end of the unitary imaging fiber optic array. It is the individual spatial positioning of one or more dyes (or dye-generating substances or dye mixtures) separately upon the discrete, optic array surface which serves to identify and distinguish each dye from all other light energy absorbing dyes (or dye-generating substances or dye mixtures) concurrently disposed on the same optic array surface; and which also provides the spatial resolution among the disposed dyes which avoids and eliminates random intermixing of individual light energy photons to and from each respective dye Each spatially positioned dye (or dye-generating substance or dye mixture) disposed at an individual location on the optic array surface will react specifically with only one analyte of interest; and show evidence of such specific reactive contact by either absorbing and reflecting a portion of the light energy or absorbing light and then subsequently emitting light energy of a different wavelength in return. Such reflected or emitted light energy is conveyed via only those individual fiber optic strands directly in aligned position with the immobilized dye itself. Such conveyed light will emerge from the other optic array surface only at precisely located spatial positions and thus be distinguishable as such from other light energy conveyed by other fiber optical strands via the precise spatial positioning and the spatial resolution of the emerging light at the optic array surface. In this manner, the conventional limitations and demands of single channel optical fibers are eliminated since the strands within the imaging fiber optical array retain the spatial positioning for each of the disposed dyes. Thus, the traditional requirement for spectral resolution is removed due to the ability of the imaging fiber optical array to resolve light energy from each of the dyes spatially.

The dyes (and dye-generating substances and dye mixtures) which may be employed and disposed individually at different precise spatial positions individually upon one optic array surface of the imaging fiber optical array are all conventionally known and often commercially available. The present invention intends that all the commonly useful properties and capabilities of the various classes of light energy absorbing dyes be employed as needed or desired for the specific use or application. Merely illustrative of the many different dyes, dye-generating substances, and dye mixtures are those fluorophores, fluorescent enzyme substrates, fluorescent antibody conjugates, and chromophores listed below within Tables I and II respectively.

TABLE I

| Compounds | Excitation Wavelength (range or λ maximum) | Fluorescence emission range (λ max) |
|---|---|---|
| A. Fluorophores | | |
| Eosin | 470-530 nm | 530-580 nm (550 nm) |
| TRITC-amine | 555 nm | 570-610 nm (590 nm) |
| Quinine | 330-352 nm | 382-450 nm |
| Fluorescein | 488-496 nm | 530 nm |
| Acridine yellow | 464 nm | 500 nm |
| Lissamine Rhodamine B Sulfonyl Chloride | 567 nm | 580 nm |
| Erythroscein | 504 nm | 560 nm |
| Ruthenium (tris. bipyridium) | 460 nm | 580 nm |
| Texas Red Sulfonyl Chloride | 596 nm | 615 nm |
| B-phycoerythrin | 545,565 nm | 575 nm |
| Nicotinamide adenine dinucleotide (NADH) | 340 nm | 435 nm |
| Flavin adenine dinucleotide (FAD) | 450 nm | 530 nm |
| Carboxy Seminaphthorhodafluor | 587 nm | 640 nm |
| Naphthofluorescein | 594 nm | 663 nm |
| B. Fluorescent Enzyme Substrates | | |
| Fluorescein mono-B-D-galactopyranoside | 452 nm | 518 nm |
| Resorufin B-D-glucuronide | 468 nm | 584 nm |
| 8-acetoxypyrene -1,3,6-trisulfonic acid trisodium salt | 365 nm | 391 nm |
| Coenzyme A (1-pyrene butanoic acid)ester | 339 nm | 377 nm |
| Fluo-3: free acid [Molecular Probes. Eugene. CA] | 506 nm | 526 nm |
| Quin-2. tetrapotassium | 352 nm | 492 nm |
| C. Fluorescent Antibody Conjugates | | |
| Texas Red goat anti-mouse FgG conjugates | 590 nm | 615 nm |
| Protein A fluorescein conjugates | 480 nm | 520 nm |
| Anti-Atrazine fluorescein conjugates | 480 nm | 520 nm |
| Anti-digoxin Texas Red conjugates | 590 nm | 615 nm |

TABLE II

| Chromophores | Energy Absorbance Range (λ max) |
|---|---|
| Iron-salicylate complex | 530 nm |
| Indamine dye | 590 nm |
| INT formazon dye | |
| Hopkins-Cole dye | 560 nm |
| Quinone-imine dye | 500 nm |
| Fe (SCN)$^{-2}$ | 460 nm |
| Malachite Green | 620 nm |
| 4-bromo A-23187, free acid | 340 nm |
| Cresol red | 415 nm. acid: 570 nm. base |
| Phenolphthalein | 600 nm |
| Oxine blue | 450 nm. acid: 600 nm. base |
| diphenylcarbazone disulphonic acid | 575 nm |
| Chrome bordeaux B | 575 nm |
| Calmagite | 650 nm |
| Ninhydrin dye | 650 nm |

It will be recognized and appreciated also that the range, variety, and diversity of light energy absorbing dyes, dye-generating substances dye formulations, and dye mixtures is not dependent upon a single light source or light energy supply in order to be effective. Although light energy of determinable wavelengths is desirably provided by electrical light sources—that is, filament lamps whose bands of light energy are typically controlled and selected by filters, diffraction gratings, polarizing filters; or alternatively broken into various broad wavelengths of light energy via prisms, lenses, or other optical/spectral articles, this is not exclusively the only source of useful light energy. clearly, in various applications and circumstances chemical light energy, bioluminescence, and other less typical or conventionally employed light energy sources are deemed to also be useful. Accordingly, neither the true source nor nature of light energy photons nor the manner in which they are conveyed or otherwise caused to be created is of importance or consequence. Note also that the spatially positioned dye individually may comprise other materials and chemical compounds for photo reactive contact. Thus each spatially positioned dye individually may in fact be formulated as a mixture of both light emitting and light absorbing dyes;, and also comprise a variety of other light energy sensitive compounds made conventionally which are able to interact with specific dye properties. Merely exemplifying the nature of such multiple dye formulations and combinations are those described and claimed within copending U.S. patent application No. 294,175 filed Jan. 6, 1989 entitled "Fluorescence Intramolecular Energy Transfer Conjugate Compositions And Detection Methods"; as well as the compositions described within U.S. Pat. No. 4,822,746 issued Apr. 18, 1989—the texts of which are individually expressly incorporated by reference herein.

Dye Deposition And Immobilization

When depositing the individual dye(s) (or dye-generating substances or dye mixture at precisely spatially positioned locations on one optical array surface, it is necessary that the dye formulations remain immobilized at the respective spatial positions assigned to each of them individually without migrating towards any other position. Multiple methods of dye deposition and immobilization are conventionally known. Thus, one may prepare a specific fluorescent or colorimetric dye formulation comprising one or more dyes and other chemical compounds; and dispose the dye formulation at a specific spatial position and location on the optical array surface. Among the conventional practices of dye deposition a variety of polymerization processes are known, including thermal techniques, ionization methods, plasma methods, and electroinitiation procedures. These different methodologies are exemplified by the following publications, the text of each being expressly incorporated by reference herein. Thermal methods: Graham et al., *J. Org. Chem.* 44: 907 (1979); Stickler, M. and G. Meyerhoff, *Makromal. Chem.* 179: 2729 (2729 (1978); and Brand et al.; *Makromol. Chem.* 181: 913 (1980). Ionization methods: A. Chapiro, *Radiation Chemistry of Polymer Systems* Chapter IV, Wiley - Intersciences, Inc., New York, 1962; J. E. Wilson, *Radiation Chemistry of Monomers, Polymers, and Plastics*, Chapters 1-5, Marcel Dekker. New York, 1974. Plasma Methods: Yasuda, W. and T. S. Hsu, *J. Polym. Sci. Polym., Chem. Ed.* 15: 81 (1977); Tibbett et al., *Macromolecules* 10: 647 (1977). Electroinitiation methods: Pistoria, G. and O. Bagnarelli, *J. Polym. Sci. Polym., Chem. Ed.* 17: 1001

(1979); and Philips et al., *J. Polym. Sci. Polym., Chem. Ed.* 15: 1563 (1977). The preferred method of dye deposition and immobilization is via the process known as photoactivation; and employs one or more photoactivated monomer preparations in admixture with one or more prechosen light energy absorbing dyes as a photopolymerizable formulation. Such monomer preparations typically comprise solutions of several monomers in admixture and a concentration of at least one light energy absorbing dye conjugated to an organic carrier which can be chemically cross-linked. A representative listing of different monomer compositions suitable for preparing an admixture which subsequently can be photopolymerized are given by Table III; and an illustrative listing of conjugated dyes ready for admixture and photopolymerization is given by Table IV below.

TABLE III

| A. Monomers |
| --- |
| acrylamide |
| N,N-methylene bis(acrylamide) |
| hydroxyethylmethacrylate |
| styrene |
| vinyl acetate |
| N-(3-aminopropyl) meth-acrylamide hydrochloride [Kodak, Inc.] |
| B. Comonomer with dimethylsiloxane |
| (acryloxypropyl) methyl (15-20%) |
| (aminopropyl) methyl (3-5%) |
| (methacryloxypropyl) methyl (2-3%) |
| C. T-structure polydimethylsiloxanes |
| methacryloxypropyl (25-50%) |
| vinyl (50-75%) |

TABLE IV

| Conjugated dye |
| --- |
| acryloyl fluorescein |
| acryloyl rhodamine |
| acryloyl eosin |
| phenol red |
| acryloyl 8-hydroxypyrene 1,3-disulfonic acid |
| acryloyl seminaphthorhodafluor |
| acryloyl seminaphthofluorescein |

It will be appreciated that the listings of Table III and Table IV are merely representative of the many different compositions which can be usefully employed in admixture with one or more light energy absorbing dyes. In addition, the scientific and industrial literature provides many alternative monomer preparations and admixtures which are also suitable for use in making the present invention. Accordingly, all of these conventionally known monomer preparations are considered to be within the scope of the present invention.

II. A Preferred Method of Making the Fiber Optic Sensor

To demonstrate a most desirable method of making the unique fiber optic sensor comprising part of the present invention; and as a demonstration of the utility and effectiveness for making optical determinations using the fully constructed fiber optic sensor, a detailed description of the manipulative steps for making a sensor able to concurrently measure both pH and oxygen concentration is presented. It will be expressly understood, however, that the detailed description which follows hereinafter is merely illustrative and representative of the many different kinds of sensors which can be made having one or more dyes disposed at precise spatial positions on one optical array surface, each disposed dye being able to specifically react with and detect one analyte of interest in a fluid sample. The dyes employed as described herein have been chosen for their ability to detect and accurately measure analytes which are correlated with changes in pH and changes in oxygen concentration.

Surface silanization

Initially, an imaging fiber optic array similar to that illustrated by FIGS. 6-8 respectively was obtained from commercial sources [Applied Fiber Optics, Inc., Southbridge, Mass.]. One optical array surface was submerged in a 20% solution of 3-(trimethoxysilyl) propylmethacrylate dispersed in dry acetone and allowed to soak for 2 hours duration. After silanization, this optical array surface was rinsed first with dry acetone and then with distilled water. The prepared optical array surface of the imaging fiber optic array was used within one hour's time in the photopolymerization process.

Imaging fiber connections

A fiber optic connector and ferrule (AMP, Inc., Harrisburg, Pa.] were modified to physically secure the imaging fiber optic array to a fiber optic cable able to transport light energy of varying wavelengths to precise spatial positions on the distal array surface of the imaging fiber optic array. The exterior surface of one desirable lighting cable is illustrated in an enlarged view by FIG. 9; and the corresponding face of one optical array surface is presented in enlarged view by FIG. 10.

Figure 9:
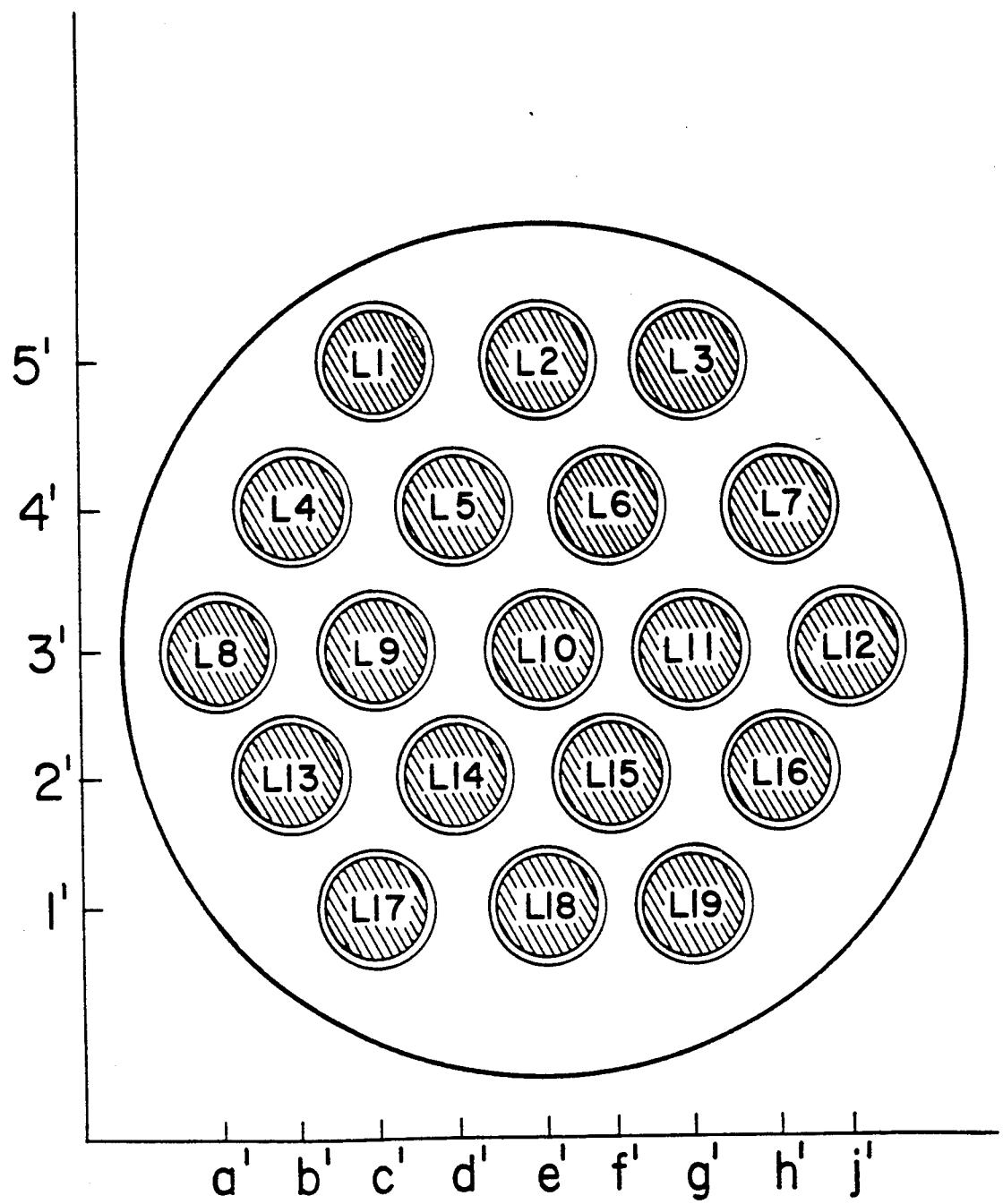
FIG. 9 is a frontal view of an illumination source able to provide light energy at precise spatial positions concurrently.

A comparison of the lighting cable surface shown in FIG. 9 reveals (in an overexaggerated, highly simplified view for purposes of clarity) that the individual light sources correspond to precise spatial positions via coordinated numerals and are directly aligned with individual fiber optical strands S1–S19 (which also are precisely positioned spatially and identifiable via linear coordinates). Thus, light originating from source L1 will be introduced only to fiber S1 spatially positioned at coordinate number 5A; similarly, light energy emanating from source L17 positioned at 1'c' will travel and be introduced only to that precise spatial position on the proximal optical array surface identifiable as coordinates "1c" and optical fiber S17. In this manner, only predetermined and prechosen fiber optical strands will receive light energy of determinable wavelengths for a specified duration; at a time desired by the user alone; and no other optical fiber strand will receive any light energy whatsoever other than those strands located at a precise spatial position on the surface of the distal array surface. By purposeful choosing, therefore, of which light sources on the lighting cable are to be employed, the user may introduce light energy at will to only prechosen, precise spatial positions and only to those few fiber optical strands known to be present at precisely that location alone on the optical array surface.

In most practical use instances, however, the lighting cable of FIG. 9 will not be employed because of the illustrated one-to-one correspondence and alignment between one light source on the face of the cable and a single fiber optical strand within the imaging fiber optic array. Recognizing that the typical cross-sectional diameter of a single fiber optical strand is only 5–500 micrometers; and recognizing further that the dye to be deposited precisely at a known spatial position on the optic array surface will desirably provide and encompass a surface area far greater than the diameter of a single fiber strand; then clearly it is impractical and unnecessary to employ only a lighting cable of such limited correspondence as that shown within FIG. 9.

In actual practice, therefore, a lighting cable was employed in the making of the pH and oxygen sensor hereof having only one light source of variable energy wavelengths rather than a cable having multiple light sources; and the single light source introduced light energy to several dozen individually clad, optical fiber strands simultaneously—all the illuminated strands being adjacently positioned within the imaging fiber optic array at precisely known spatial positions. In this manner, the single light source corresponds to and aligns with multiple fiber strands simultaneously; and permits the deposition of a dye over multiple strand faces simultaneously. The advantages and benefits of using the single source lighting cable are that a greater surface area of dye is obtained for reactive contact and a greater (but controlled) volume of dye is precisely deposited at the prechosen spatial position on the optic array surface with minimal time and labor.

The lighting cable of FIG. 9, although completely operational and functional for its intended purpose, is provided merely to demonstrate the principle of introducing light energy to a precise location on the proximal optic array surface; and to demonstrate the manner in which the dye becomes photopolymerized and precisely positioned at a prechosen location on the distal optic array surface. Having illustrated both the principle and the intended result, it will be recognized and appreciated that any lighting source of any correspondence with the fiber optical strands of the imaging fiber optic array will serve so long as the disposed dyes are spatially separate and spatially distinguishable from one another on the optic array surface.

Monomer preparations

The pH sensing dye admixtures were formulated as follows: Aqueous solutions of 5.63M acrylamide and 0.0746M N,N-methylene bis(acrylamide) were prepared in phosphate buffer solution (pH 6.6). A typical stock solution comprised 5.0 mls of bis(acrylamide), 3.0 mls of acrylamide, 5.0 mg of riboflavin, 10 mg of acryloyl fluorescein, preferably prepared in a glass container. The stock solution is adjusted to pH 6.6 using 0.1M NaOH or HCL. The stock solution was then deoxygenated by bubbling molecular nitrogen into the prepared mixture for one hour's duration. In addition, a fresh catalyst solution was prepared by dissolving 40 mg of ammonium persulfate in 0.50 ml of pH 6.6 phosphate buffer. Subsequently, the final admixture is made by combining 3.0 ml of the stock solution and 0.5 ml of the prepared catalyst solution.

As a useful and desirable alternative monomer preparation, the individual solutions are prepared as described previously above, except that 2 mg of acryloyl tetramethylrhodamine may be substituted for the 10 mg of acryloyl fluorescein.

Oxygen sensing dye admixtures:

The oxygen sensing dye admixtures were formulated as follows: 10 ml of methylacryloxypropyl T-structure [Petrarch Systems, Bristol, Pa.] was combined with 100 mg of camphorquinone in 1.0 ml of methanol and 10 mg of tris (2,2'-bipyridyl ruthenium (II) chloride hexahydrate [Aldrich Company, Milwaukee, Wisc.] in 1.0 ml of methanol. This prepared stock solution was then deoxygenated by bubbling molecular nitrogen through the preparation for one hour's duration. Approximately 3.0 ml of the prepared stock solution was then employed for polymerization purposes.

Photopolymerization

The manipulations performed during photopolymerization are illustrated via FIGS. 11-16 respectively. For descriptive purposes only, the greatly magnified and oversimplified construction of the optic array surface of FIG. 10 and the lighting cable of FIG. 9 will again be used.

Figure 10:
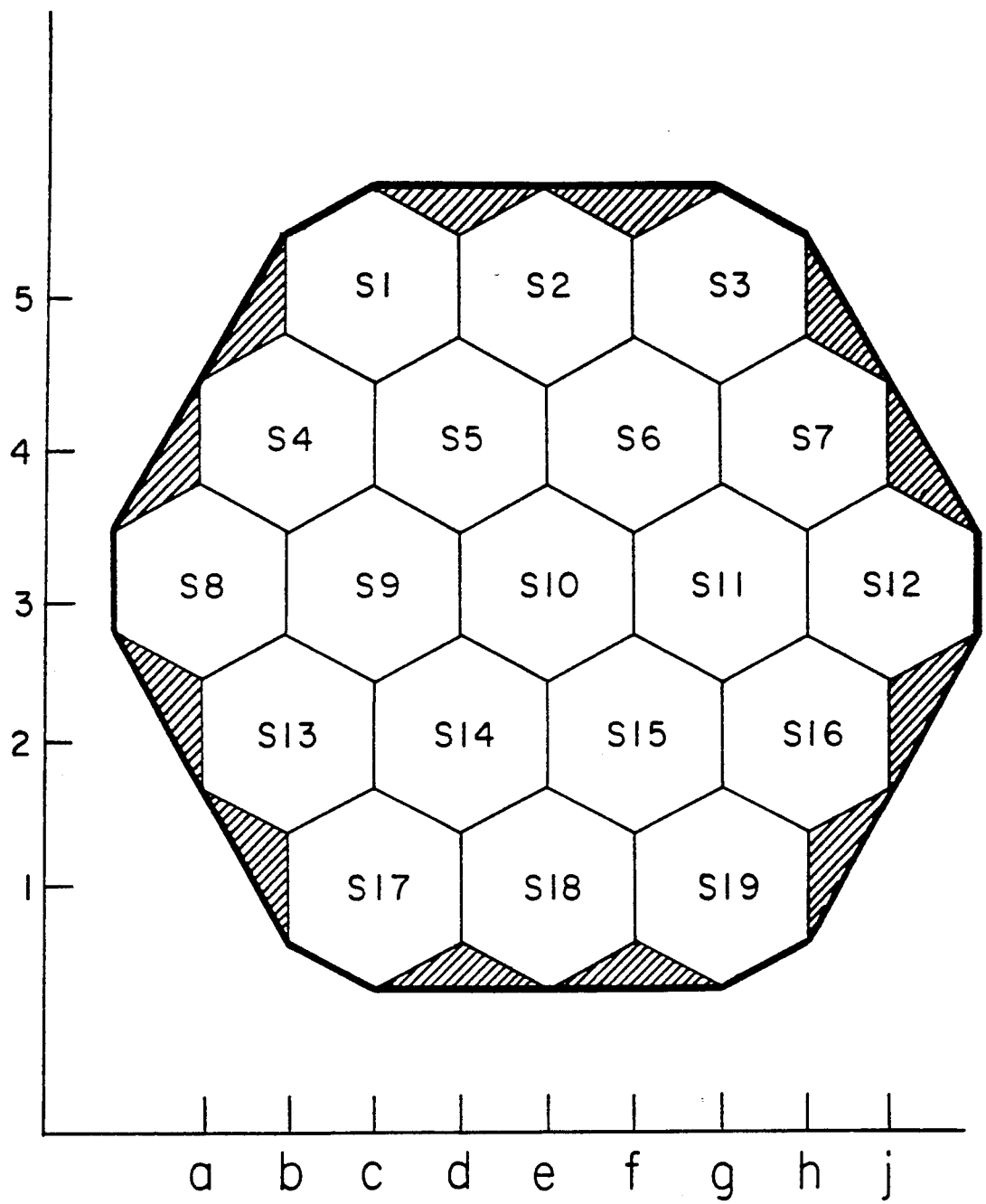
FIG. 10 is a magnified view of the optic array surface of FIG. 7B for the introduction of light energy at precise spatial positions.
Figure 11:
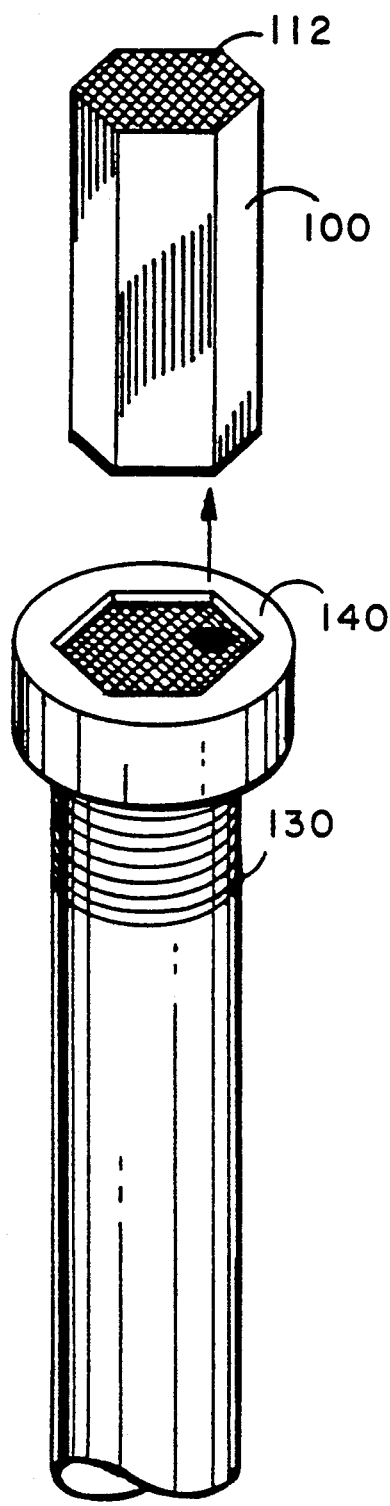
FIGS. 11-16 illustrate the manipulative steps performed during the deposition of photopolymerized dyes individually at precise spatial positions on one optic array surface of the imaging fiber optic array of FIG. 6.
Figure 12:
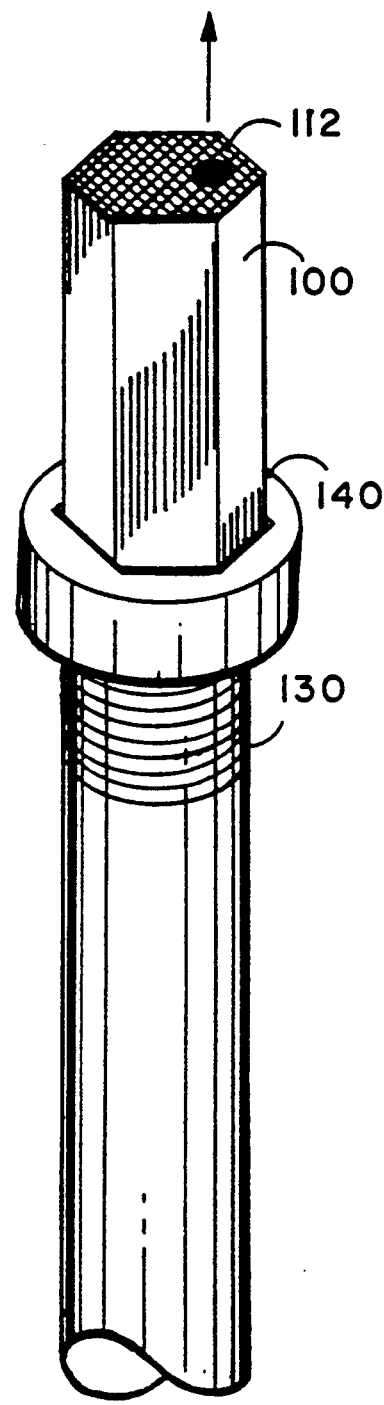

As seen within FIGS. 11-16, a fiber optical connector 130 and illumination source 140 provide the capability for illuminating specific areas of one optic array surface of the imaging fiber optic array described previously. Thus, the light energy photons emanating from the surface of the illumination source 140 within FIG. 11 are produced by only light sources L13, L14, and L17 respectively of FIG. 9. Only light energy at that precise spatial position is directed towards the distal array surface 114 of the imaging fiber optical array 100. Consequently, as shown previously via FIG. 10, only those fiber optical strands located at spatial position coordinates 2b, 2d, and 1c respectively fibers S13, S14, and S17) receive the light energy photons then provided by the illumination source 140. Consequently, as illustrated by FIG. 12, only those individually clad fiber optical strands (S13, S14, and S17) convey the introduced light energy through the body of the imaging fiber optical array 100; and the light exits at the distal optic array surface 112 only at precise spatial positions—that is, solely at coordinate numbers IIB, IID, and IC as seen within FIG. 8A above. It will be recognized and appreciated that no other spatial positions on the proximal array surface 112 are illuminated during this manipulation.

Figure 13:
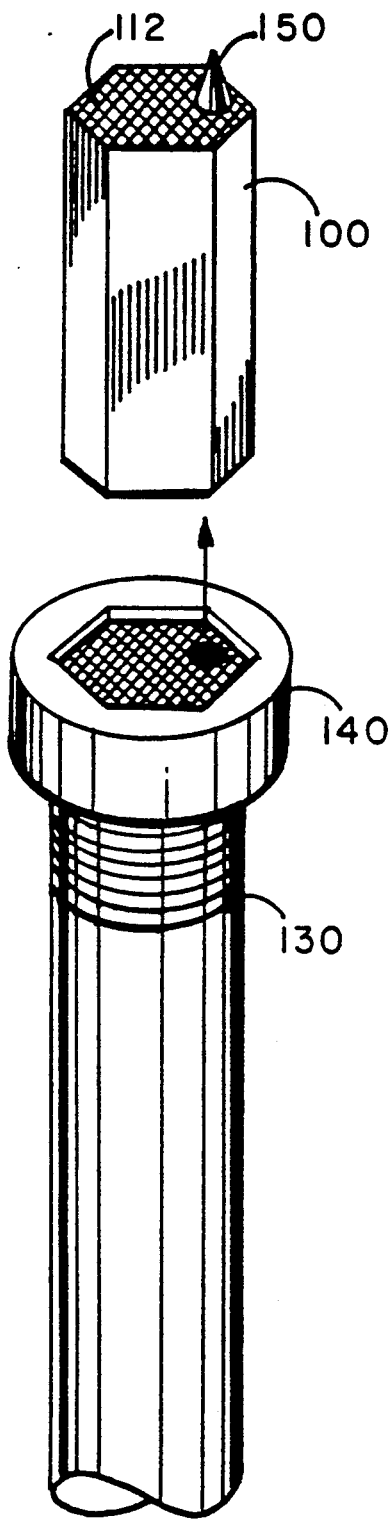

A The first polymerization step:

When the light energy photons exit from the distal optic array surface 112 at only the precise spatial positions indicated by FIG. 12, the distal optic array surface lies submerged in the prepared pH sensing dye monomer admixture comprising acryloyl fluorescein. The light employed at only this precise spatial positioning zone employed was 460 nm light and the optic array surface was allowed to react with the monomer preparation for approximately 45 minutes duration. The reactive contact between the pH monomer admixture and the 460 nm light initiated a photopolymerization reaction on the distal surface which caused a deposition and an immobilization of the fluorescein dye only at those illuminated spatial positions on the proximal array surface. Thus as shown by FIG. 13, at the end of the allotted reaction time for photopolymerization, a discrete cone-shaped volume 150 of polymerized fluorescein dye was deposited and immobilized solely on the optic array surface at only these precisely identifiable positions; and the dye's position is exactly identifiable and distinguishable from all other spatial positions on the optic array surface using the numerical coordinate system. It will be appreciated also that that the remainder of the monomer admixture does not polymerize.

It must be remembered, however, that FIG. 10 presents a highly simplified illustration of an optic array surface; provides only 19 fiber strand faces cumulatively; and moreover, that the amount of cladding material surrounding each of the fiber optic strands within FIG. 10 is intentionally omitted for added clarity and ease of understanding. In actual practice and fact, however, there typically are almost one million fiber strands per square millimeter of imaging fiber optic array; and the thickness of cladding material surrounding the fiber strands is so minimal as to require extremely high magnification in order to be seen at all. The density of fiber strand diameter is so overwhelmingly greater than the corresponding cladding material that there is virtually no effective space between the individual fibers within the imaging fiber optic array despite the existence and presence of the cladding material. Consequently, when the dye preparation becomes photopolymerized and is deposited upon the optic array surface, the dye is disposed as a single, discrete volume or cone which covers and encompasses the faces of multiple fiber optic strands as a unit.

Figure 14:
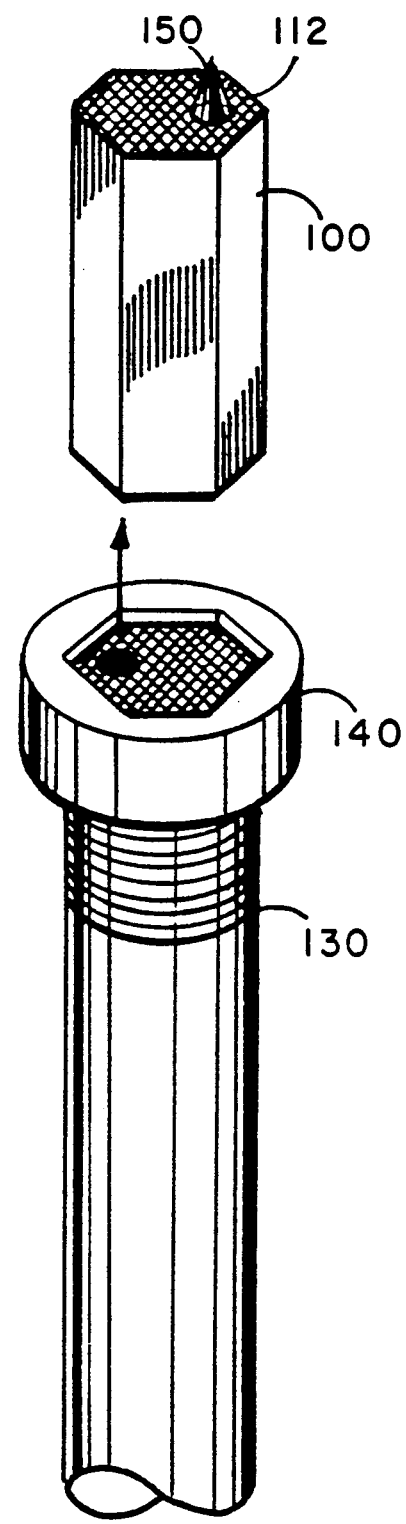

The second polymerization step:

After the first polymerization has been completed as described, the illumination source 140 was then used again to illuminate a different set of light sources corresponding to light positions L1, L4, L5. Light energy from only these light sources introduced light energy photons precisely to the optic array surface only at coordinate positions 5c, 4b, and 4d. This, in turn, caused the introduced light energy photons to be conveyed solely by fibers S1, S4, and S5. No other fiber strands were illuminated and no other fiber strands conveyed any light energy whatsoever. This is illustrated by FIGS. 14 and 15.

Figure 15:
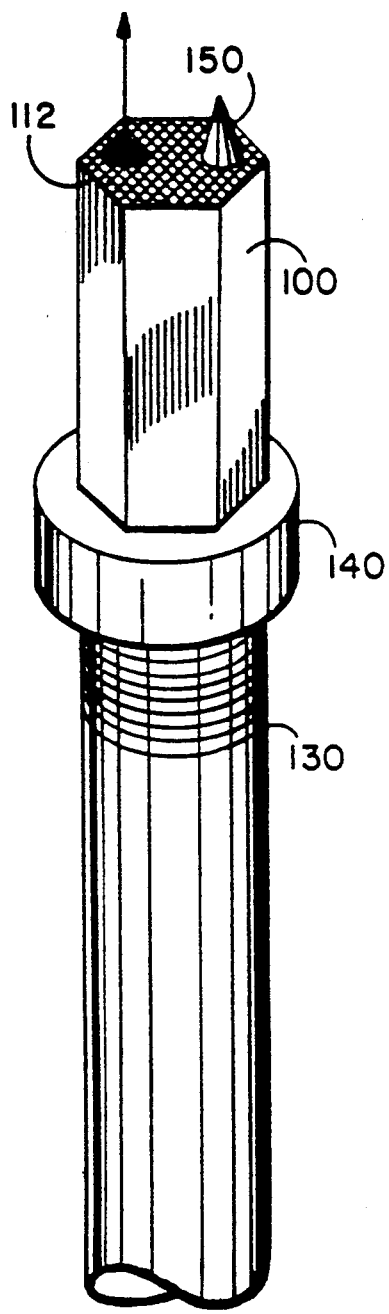
Figure 16:
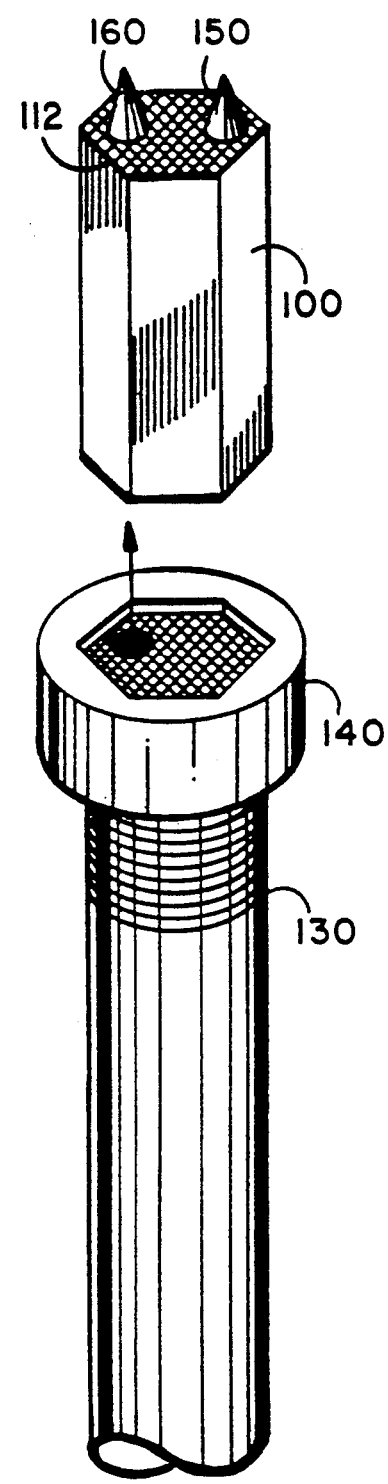

Consequently, as appears in FIG. 15, light energy photons carried by only these individually clad, fiber optical strands (S1, S4 and S5) cause the light to be conveyed and to exit from the optic array surface 112 only at coordinate position numbers VB, IVA, and IVC as illustrated by FIG. 8A. The light wavelengths appearing at only these precise spatial positions on the distal optic array surface was 460 nm. The distal optic array surface was then immersed in the prepared oxygen sensing dye monomer mixture and the light energy allowed to react with the prepared mixture for 2 hour's duration. During this reaction time, photopolymerization proceeded and the ruthenium dye in the mixture was deposited solely at those spatial positions which were illuminated. In this manner, the ruthenium dye became immobilized by photopolymerization at only those precisely locations identifiable by the coordinate numbers while the remainder of the monomer mixture did not polymerize. At the end of the allotted time for reactive contact, the distal optic array surface of the imaging fiber optic array was removed from the second monomer admixture and revealed the deposition of immobilized ruthenium dye at the precise spatial positions now identifiable precisely by coordinate numbers VC, IVB, and IVD. A discrete cone 160 of ruthenium dye could be seen extending from the distal optic array surface as illustrated by FIG. 16.

It will again be recognized and appreciated that under typical conditions the density of fiber strand diameter in the imaging fiber optic array so overwhelmingly exceeds the amount of corresponding cladding material that there is no effective physical barrier separating the fiber strands during the photopolymerization process. Thus the photopolymerization of the ruthenium dye mixture at only the prechosen and illuminated spatial positions results in the deposition of a single, unitary volume or cone of dye large enough in surface area to encompass and cover multiple fiber faces on the distal optic array surface. The presence of the cladding within the imaging fiber optic array does not effectively interfere with or hinder dye deposition. This result is both true and constant regardless of what specific process for depositing dyes is employed and whether or not the favored photopolymerization technique is used.

The practitioner ordinarily skilled in this field will by now also recognize that there is no requirement or demand that an illumination fiber as such be employed in this photoactivated method for making the sensor. One merely needs to introduce pinpoints of light into separate portions or areas of the imaging fiber optic array for photopolymerization to proceed. Thus, for example, one could achieve equivalent effects using lenses and/or lasers. Accordingly, any conventionally known means or manner of introducing light is within the scope of the present invention.

Figure 17:
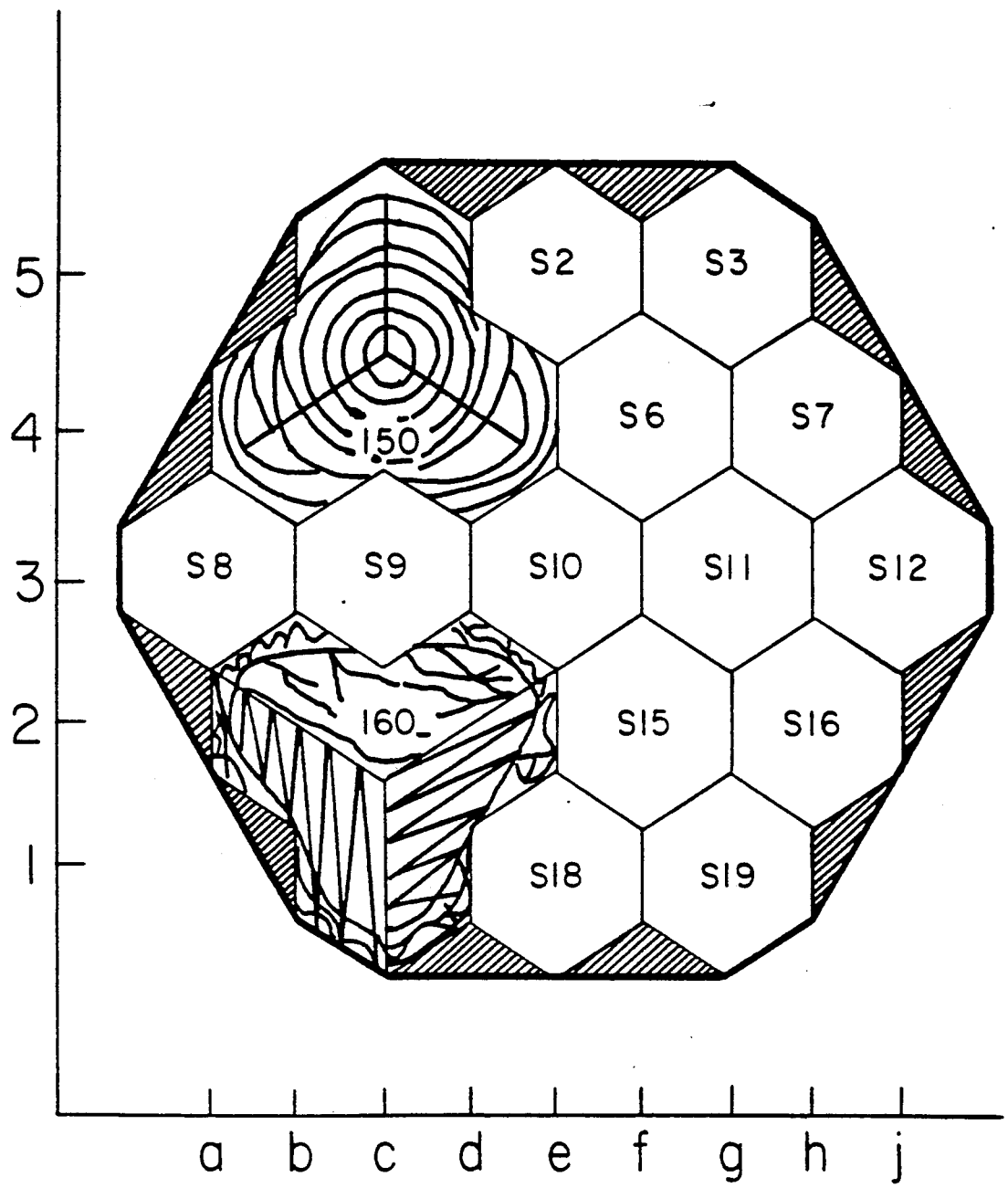
FIG. 17 is an overhead view of the one optic surface of the constructed fiber optic sensor.

The results of the completed photopolymerization process are illustrated by FIG. 17 in which the polymerized cone of fluorescein 150 and the polymerized cone of ruthenium dye 160 are individually located and identifiable at precise spatial positions on the optic array surface. It will be recognized that much of the optic array surface 112 remains unencumbered and unobscured and that light introduced at the proximal array surface 114 at these unobscured spatial positions would be conveyed and exit from the distal optic array surface as unencumbered light photons which do not effect or influence the dye cones 150, 160 positioned separately nearby. In turn, light introduced at the proximal optic array surface 114 and conveyed via only those fiber optical strands aligned directly beneath each polymerized cone of dye alone will consequently illuminate either the fluorescein dye cone 150 or the ruthenium dye cone 160 independently and concurrently. Thus by illumination of only precise spatial positions on the distal array surface, the user may illuminate either one of the polymerized dyes on the optic array surface without involvement of the other distinctly and precisely positioned cones of polymerized dye.

III. Detecting Apparatus Employing the Unique Fiber Optic Sensor

Figure 18:
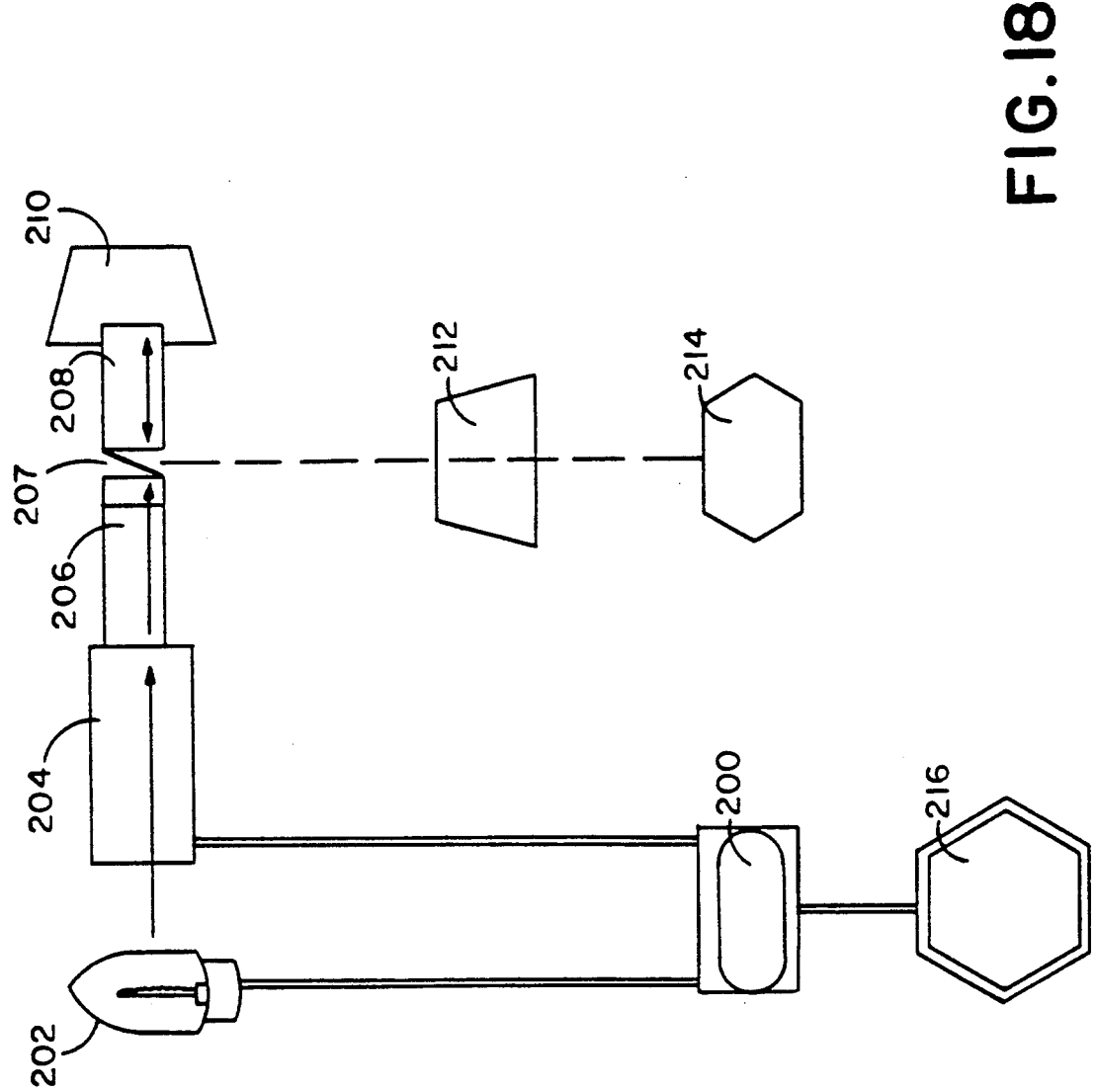
FIG. 18 is a block schematic illustration of the automated apparatus comprising the fiber optic sensor of FIG. 17.
Figure 19A:
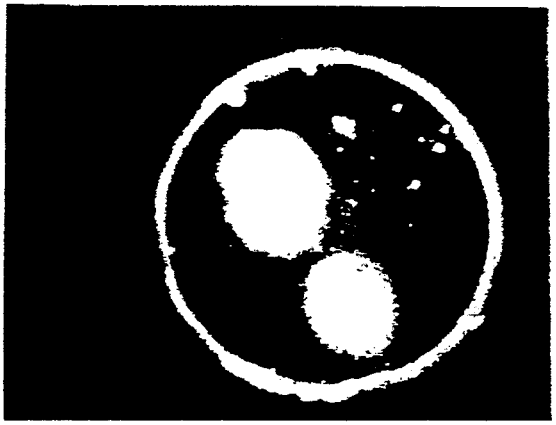
FIGS. 19A-19D are imaging photographs of the immobilized dyes disposed on the distal optic surface of the fiber optic sensor after illumination using the apparatus of FIG. 18.
Figure 19B:
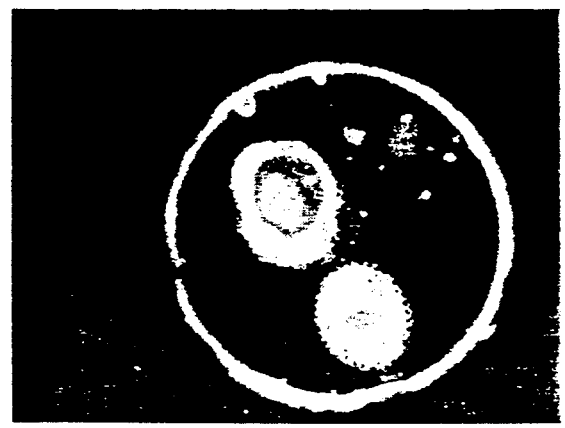
Figure 19C:
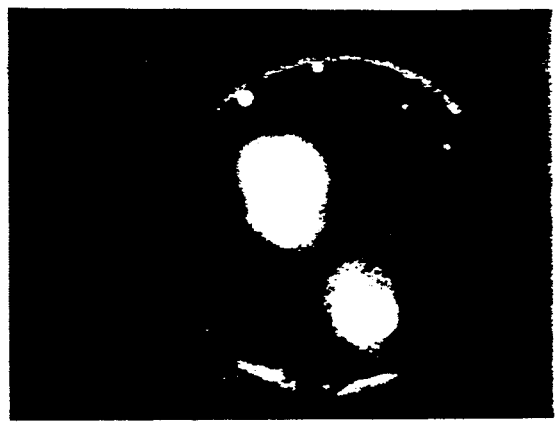
Figure 19D:
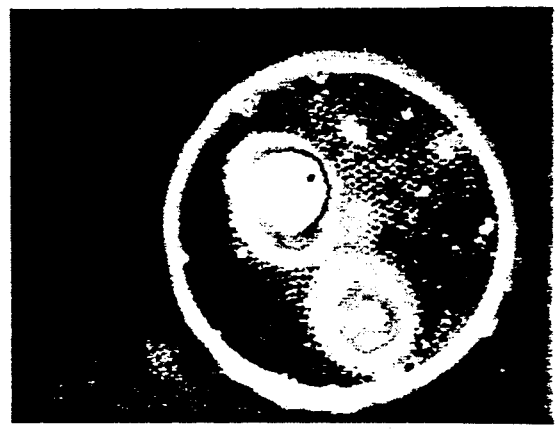

A preferred fully automated, computer controlled, apparatus and detection system is illustrated in block format by FIG. 18 in block format. As seen therein, a controller 200 serves to generate and control an image processing and detection system from the generation of light energy photons of a specific wavelength to the control and detection of optical images then measured in both qualitative and quantitative parameters. Such controllers are commercially available and provide software and hardware with a microprocessor and computer which allows the entire apparatus to be controlled from a single keyboard. Such a commercially available controller is the QX-7 image processing system [Quantex, Inc.] which provides monitors for both visual display and mathematical calculation of the optical data empirically detected and measured. The controller 200 controls a high-intensity light beam 202 which passes through a first monochromater or filter 204 for the selection of light energy of a predetermined wavelength. The controller 200 then causes the first light energy photons to be directed via an optional fiber optic cable 206 and a mirror or dichroic filter 207 to the proximal optic array surface of the fully constructed fiber optic sensor 208—which has one or more light energy absorbing dyes immobilized individually at separate and distinct precise spatial positions on the distal optic array surface. The distal optic array surface of the fiber optic sensor 208 has been placed in a sample holder into which a fluid sample is introduced for reactive contact with the distal optic array surface of the fiber optic sensor. The introduced light illuminates the dye which has reacted with the analyte of interest within the sample holder 210.

As a result of the reactive contact between the dye disposed on the distal optic array surface of the fiber optic sensor 208 and the fluid sample in the holder 210 light energy emanating from the dye (by emission or reflection) is then conveyed through the fiber optic strands in the fiber optic sensor 208 and emerges at the proximal optic array surface as emergent light energy. The apparatus is desirably constructed such that the emergent light energy is deflected via the mirror or dichroic filter 207 and observed at right angles to the original incident beam of introductory light. The emergent light energy then passes through a second monochromater or filter 212 for wavelength analysis; and then falls upon a photosensitive detector 214 for qualitative and quantitative measurement of the photons present as the emerging light energy. The detector 214 typically is a camera. The detector 214 also is in direct contact with the controller 200 which mathematically calculates and plots the intensity of the emerging light as a function of its wavelength and quantum of photons present. This data and mathematical calculation is then preferably seen visually on a monitor display 216 which can provide a visual image of the dye reacting with the individual analyte of interest; and can also provide the empirical data in raw or mathematically calculated and correlated formats.

In many instances, the sample holder 210 will optionally permit inclusion of a microscope or camera apparatus in addition to providing an enclosed chamber for reactive contact between the immobilized dye on the distal optic surface of the fiber optic sensor and the analyte of interest in the fluid sample. Many other instruments may be optionally added at various positions in the automated system to provide detailed information as the user requires or desires.

It is also optionally available for the user to operate the image processing and detection apparatus and system manually at one or more positions if this is desired. Alternative assemblies may be erected in which the entire series of manipulative steps may be done manually for specific purposes of the experiment or analysis. In most instances and for general operation purposes, however, the fully automated, computerized imaging and process system as described herein is most desirable.

The apparatus illustrated in block format via FIG. 18 intends that the light energy be introduced and conveyed concurrently (simultaneously or sequentially) to each of the individual dyes disposed on the distal optic array surface of the fiber optic sensor. The true value and benefit of the fully automated apparatus and image processing system is that light energy of the same or different wavelengths will be precisely introduced concurrently (simultaneously or sequentially) at the proximal optic array surface of the optic fiber sensor; that only pre-identified and chosen fiber optical strands will convey that individual light energy to one immobilized dye situated precisely at a single spatial position on the distal optic array surface of the sensor after reactive contact with a fluid sample; and that the emerging light from each immobilized dye after reactive contact with its own individual analyte of interest would then be recognized via its emergence from only precise spatial positions which allow it to be detected and measured independently without interference in the shortest possible time period. The fully automated, computer controlled system thus allows multiple determinations, measurements and detections to be made within fractions of a second concurrently, simultaneously or sequentially without accidental mixing or interferences between the emergent light at different spatial positions on the proximal optic array surface of the fiber optic sensor. The controller then identifies and quantifies the light emerging at each precise spatial position; and is able to mathematically calculate and correlate the light energy data with specific parameters in order to provide meaningful determinations for specific assay purposes.

IV. Empirical Measurements and Data Using the Improved Fiber Optic Sensor and Detection Apparatus Using the constructed fiber optical sensor having both a photopolymerized fluorescein dye at one precise spatial position and a photopolymerized ruthenium dye at a second precise spatial position on the distal optic array surface of the optic sensor, the ability to utilize each of these dyes individually at their own specific wavelengths of light energy will be demonstrated. The photopolymerized fluorescein dye is employed for the measurement of pH in accordance with the procedure described within Munkholm et al. [*Anal. Chem.* 58:1427 (1986)], the text of which is expressly incorporated by reference herein. Similarly, the photopolymerized ruthenium dye is employed for measurement of oxygen concentration in a fluid sample using the procedure described by Wolfbeis et al, [*Anal. Chem.* 60:2028 (1988)], the text of which is also expressly incorporated by reference herein. This purposefully prepared fiber optic sensor able to detect and measure both pH and oxygen concurrently is employed within the apparatus previously illustrated within FIG. 18 using the fully automated, computerized imaging and processing system described therein.

As regards the nature of the immobilized fluorescein and ruthenium dyes disposed at precise spatial locations on the distal optic array surface of the fiber optic sensor, the spectral properties of these dyes are recognized as fluorophores having overlapping excitation light wavelengths and moderately overlapping emission light wavelengths as indicated within Table I previously herein. Alternatively, if the user wishes, one or more other dyes having identical excitation light and emission light wavelengths could also be employed without difficulty due to the spatial resolution of light energy provided by the fiber optic sensor.

Experiment 1: Visualization of the Individual Immobilized Dyes

To demonstrate the ability to visualize and employ the immobilized dyes disposed precisely at individual spatial positions on the distal optic array surface of the fiber optic sensor, the emerging light energy from each of the pH and oxygen sensing dyes after introduction of exciting light was detected and processed as an image using the controlled image processing system of the automated apparatus. The images were then visualized via television monitor displays using the computerized control system. Subsequently, slight variations in excitation light wavelengths were employed in order to determine whether a better or worse visualized image could be obtained by the computer processing imaging system. The results of using slightly different wavelengths of exciting light energy conveyed specifically to a precise spatially positioned dye are provided by FIGS. 19A-19D respectively.

As shown therein, the detected emission light wavelengths from each dye individually were processed and appeared as complete images on the television monitors and revealed two distinct substantially circular immobilized dye images which correspond in location to the specific numerical coordinates for each specifically positioned dye individually. As noted by the differences in image intensity and background noise on the monitor displays, the intensity of the visualized light images varies somewhat depending on the operating conditions of the automated system. Nevertheless, each dye is clearly and distinctly visible; provides variances in emission light energy; and is identifiable and distinguishable from the other on the basis of its precise spatial positioning on the distal optic array surface of the fiber optic sensor.

Experiment 2: Contour Intensity Plots

A second experiment was conducted in accordance with the procedure described for Experiment 1 above, in which the detected and measured emission light wavelengths from each of the immobilized dyes at individual spatial positions on the distal optic array surface of the fiber optic sensor were processed as a contour plot to determine the intensity as a visual display. The computerized software program permits such graphic displays to be visualized on a television monitor using the emission light from each dye after excitation. Accordingly, exciting light energy was introduced to the proximal optic array surface and then conveyed by fiber optical strands within the fiber optical sensor to each of the immobilized dyes individually on the distal optic array surface; and the emitted light as seen at the distal optic array surface (not the proximal surface) was detected and measured directly using the computerized imaging processing automated system. The results are visualized and displayed on a monitor as shown by FIGS. 20A and 20B respectively.

A close inspection of FIG. 20A in particular shows the location of each photopolymerized dye at an individual spatial position on the distal surface; and shows each disposed dye to be involved in the discharge of the emitted light. FIG. 20B also shows each photopolymerized dye individually to be involved during the absorbance of exciting light wavelengths and the subsequent discharge of emitting light wavelengths. These contour plots of light intensity reveal that the photopolymerized dyes themselves maintain their positional and spatial integrity during use; and are able to display their own characteristic light absorbing and light emitting properties by being held in adjacent position at precise locations on the distal optic surface of the fiber optic sensor.

Experiment 3: Empirical Measurement of pH Values

The fiber optic sensor prepared as previously described was placed in a sample holder and subjected to reactive contact with different fluid samples in series, each fluid sample being specifically formulated at a different pH value. The individual pH values for each fluid sample were: pH 5; pH 7; and pH 8.2 respectively. Each fluid sample was individually introduced and allowed to make reactive contact with the distal optic array surface of the constructed fiber optical sensor evaluated previously in Experiments 1 and 2.

Figure 21A:
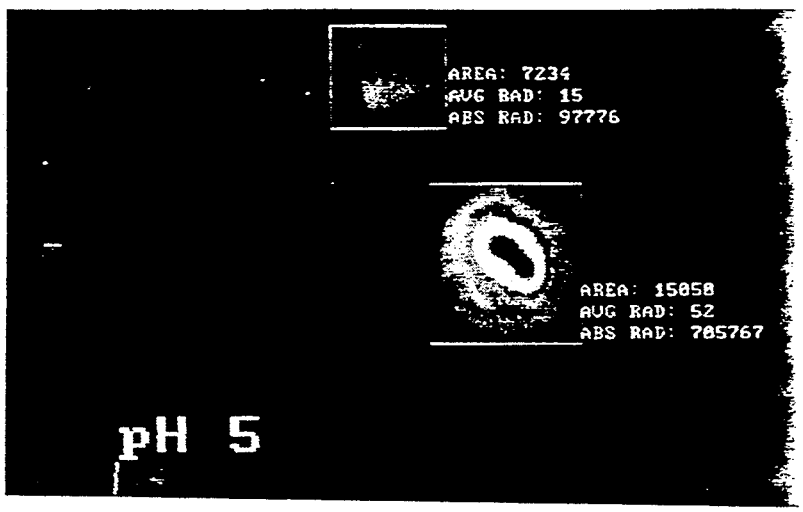
FIGS. 21A-21C are imaging photographs and data displays provided by one dye on the surface of the fiber optic sensors to measure pH values using the apparatus of FIG. 18.
Figure 21B:
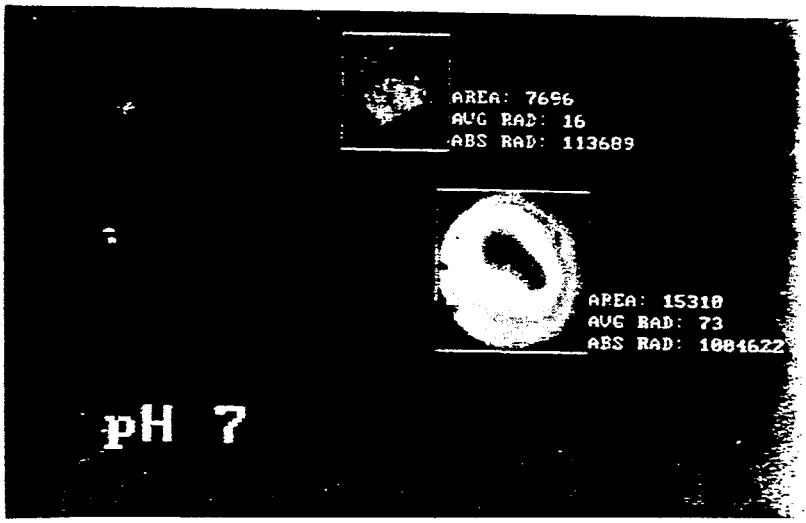
Figure 21C:
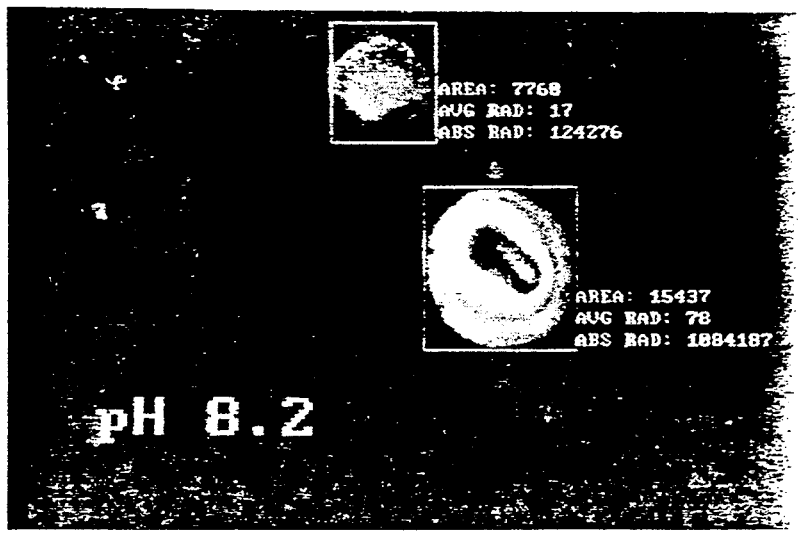

For measurement and detection purposes, only a single exciting light energy maintained at a wavelength of 488 nm was introduced to the entire proximal optic array surface and conveyed to both photopolymerized dyes disposed on the distal optic array surface. After the exciting light energy was received by the dyes at the distal surface, the subsequent emissions of light energy from the dye as observed directly at the distal surface after reactive contact with each individual fluid sample were detected, measured, and visualized on the monitors using the computerized imaging systems. The individual values and displays observed for each of the fluid samples having different pH values are shown by FIGS. 21A, 21B, and 21C individually.

It will be noted and appreciated that the computerized imaging and processing system allows the important technical data and correlations to be displayed on the monitor as well as the display of a discrete image of the illuminated photopolymerized fluorescein dye as it reacts with the fluid samples individually. Thus, the image obtained with the fluid sample known to be at pH 5 is measured and calculated to have a precise radiation value. Note also that the visual display provides information regarding the total area involved, the average radiation, and the absolute radiation in each instance. Thus, as noted by the empirical data displayed by FIG. 21, the detected and visualized raw data can be directly correlated and standardized to give precise pH values and determinations with any unknown fluid sample—using the data of FIG. 21 as a test standard. YAW, 27

It will be appreciated via FIG. 21 that the distal surface visual image displayed upon the monitor shows the presence of the dyes illuminated with a single wavelength. Even though there is moderate overlap of the dyes' emission spectrum, both dyes are discernable completely due to the spatial resolution. Nevertheless, because the exciting light used in the photopolymerization was introduced in precise locations identifiable from specific numerical coordinates; and since the only fluorescence comes from these location coordinates, there is no doubt that, the fluorescence detectable at either the distal or proximal optic array surface comes from only that dye containing polymer at that photopolymerized numerical coordinate.

Experiment 4: A pH Sensor Having Three Distinct Depositions of a Single Dye Reagent A pH sensing fiber optical sensor was constructed employing the imaging fiber optic array in which three distinct and discernible cones of a single dye reagent were immobilized on the distal optic array surface using the photopolymerization methodology previously described herein.

The pH sensing dye admixture was prepared as follows: to a 4.0 ml glass vial was added 1.0 ml of polymer stock solution (7.95M 2-hydroxyethyl methyacrylate in n-propanol), 1.0 ml of stock methylene bisacrylamide solution (0.078M methylene bisacrylamide in n-propanol), 1.0 ml of pH 5.4 phosphate buffer, 3.0 mg acryloyl fluorescein in 0.5 mls of n-propanol, and 100 mg benzoin ethyl ether in 1 ml n-propanol. The solution was deoxygenated with molecular nitrogen for 20 minutes.

By immersing one optic array surface (the intended distal surface) into this pH dye admixture and introducing light energy to different portions of the other non-immersed optic array surface (the intended proximal surface) in succession, three distinct and individually discernible depositions of the one dye reagent at precisely known spatial positions on the immersed optic array surface is achieved. The fully constructed three cone sensor is illustrated by FIGS. 22A and 22B.

Figure 22A:
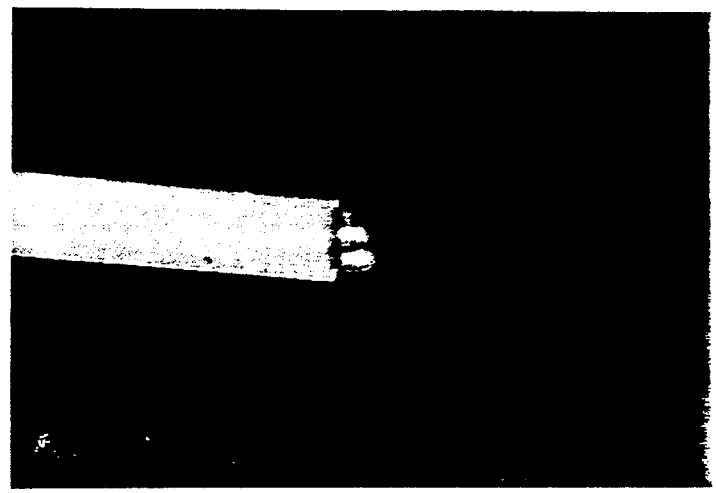
FIGS. 22A and 22B are photographic and schematic illustrations of one fiber optic sensor having three discrete pH sensitive disposition of dye reagent for sensing PH.
Figure 22B:
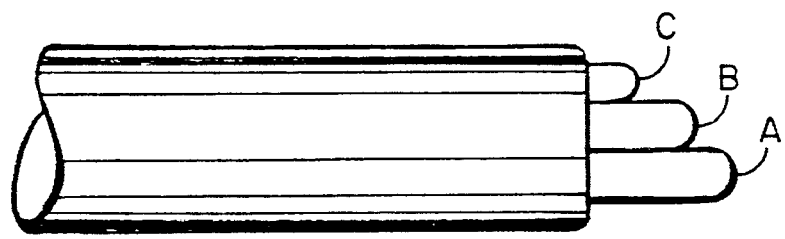

FIG. 22A shows the side-view photograph taken under a light microscope of the constructed pH sensor that has three discrete pH sensitive polymer cones protruding from its distal face. FIG. 22B is a schematic drawing identifying the cones individually. The sensor body is 300 microns in diameter. The approximate dimension of the polymer cones diameter by height) are: Cone A, 125 uM by 140 um; cone B, 125 um by 123 uM; and cone C, 125 um by 70 uM. The cone height directly corresponds to photoinitiation times: cone A, 3.5 minutes; cone B, 2 minutes; cone C, 1 minute. Short photopolymerization times result in corresponding thinner films and cone heights.

Figure 23A:
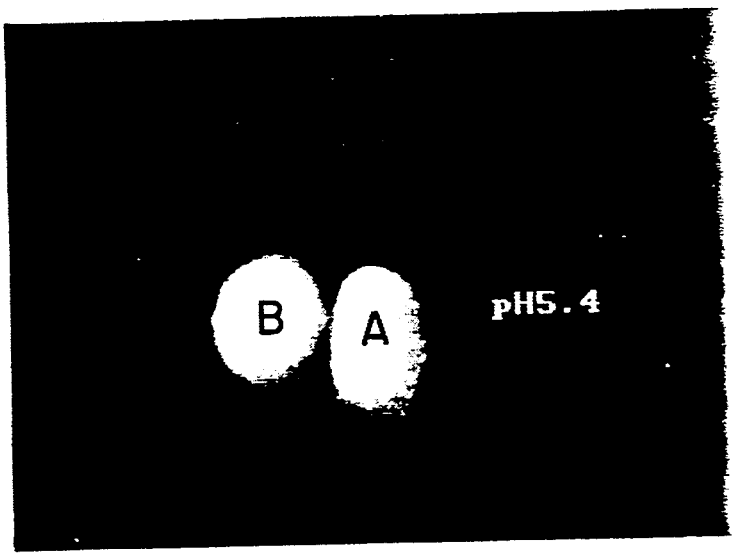
FIGS. 23A, 23B and 23C illustrate the fluorescence intensity of the pH sensor of FIG. 22.
Figure 23B:
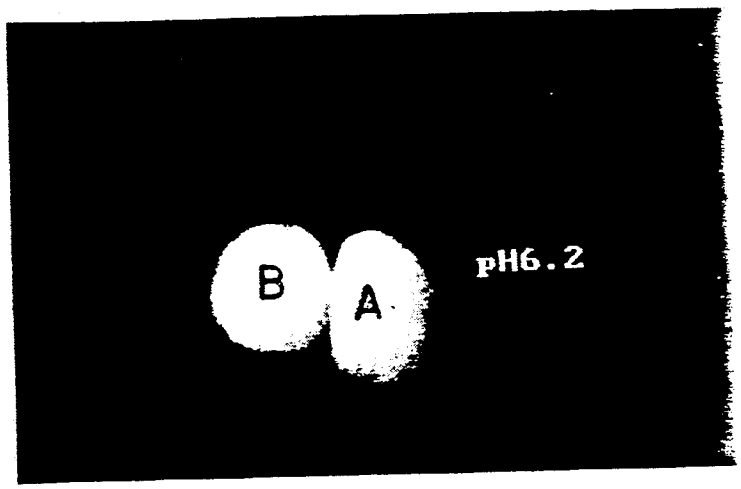
Figure 23C:
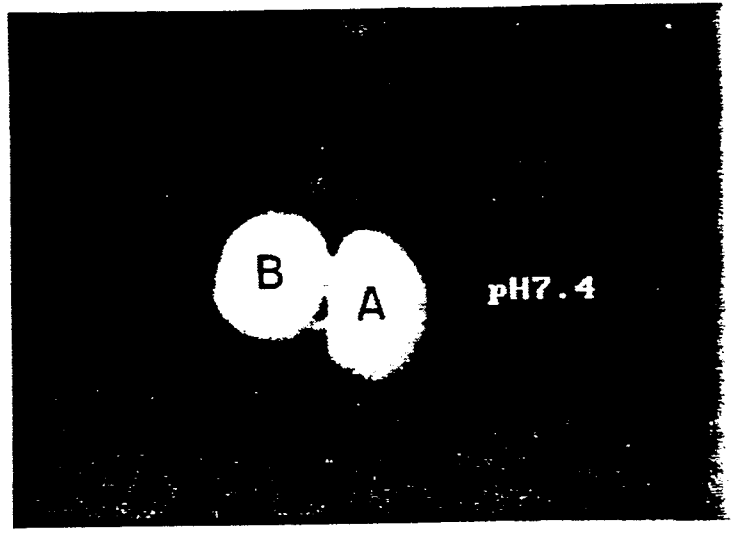

The pH sensor was tested by submerging in phosphate buffer solutions of different pH value and capturing the emitted fluorescence image with the automated apparatus using a camera. FIGS. 23A, 23B and 23C show the fluorescence intensity detected at the sensor's proximal optic surface, which is the transmitted image of the distal optic surface, containing the three individual ph-sensitive cones in pH 5.4, 6.2, 7.4, respectively. The polymer cones appear as distinctly separate fluorescent oval spots. The spots appear oval because the optic surface of the sensor was not aligned perfectly perpendicular to the camera. In pH 5.4 (FIG. 23A), cone A is not visible and cones B and C appear as coarsely-grained off-white spots. However, in pH 7.4 (FIG. 23C), all three cones' intensities increased: cone A is visible and appears as a coarsely-grained grey spot, whereas, cones B and C appear as solid opaque white spots. The increase in intensity demonstrates the pH sensitivity of the cones and is consistent with the spectral properties of fluorescein.

Figure 24A:
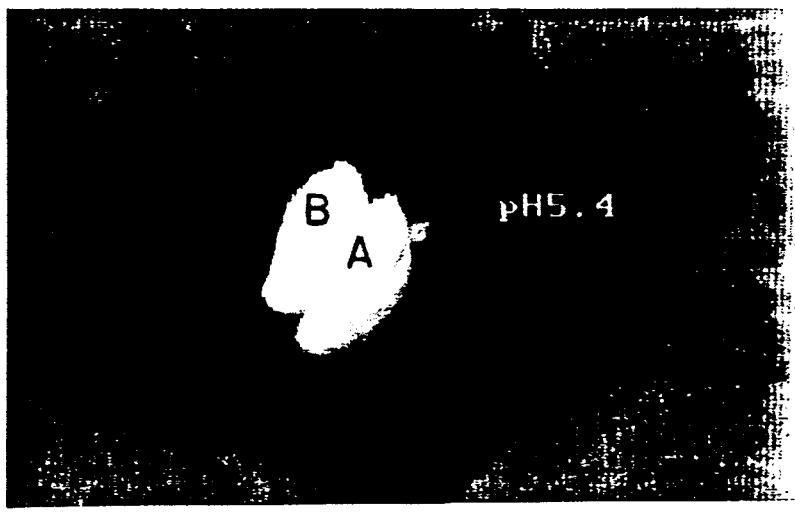
FIGS. 24A, 24B and 24C illustrate a computer generated three-dimensional analysis of the fluorescence intensity seen in FIG. 23.
Figure 24B:
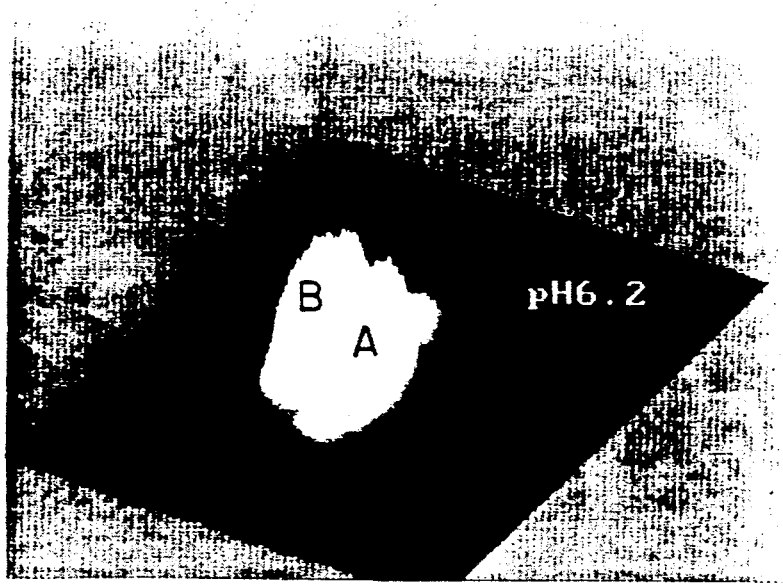
Figure 24C:
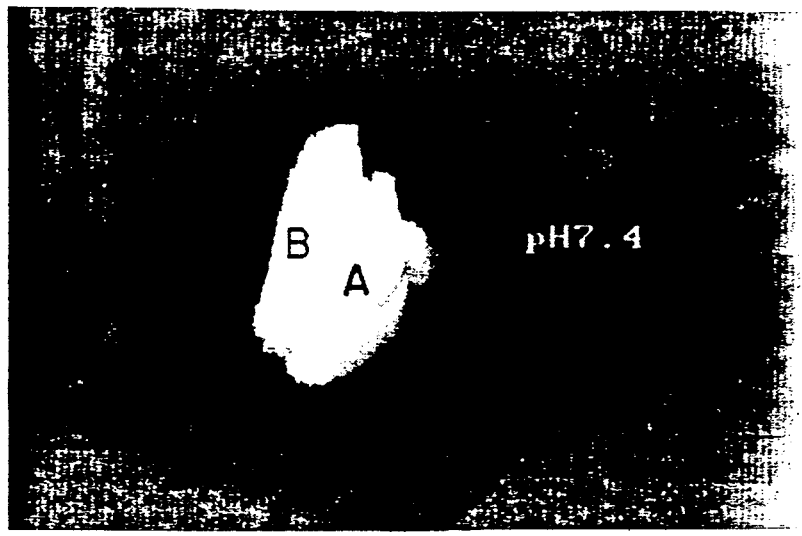

To view clearly the change in intensity of these areas, a computer generated three-dimensional analysis (x and z axes coordinate spatial position and y axis measures intensity) of the respective images was plotted as shown by FIGS. 24A, 24B and 24C. The response of the sensor to changes in pH can be seen via the increase in intensity (y-dimension) of the cones with increasing pH. In addition, color was computer-assigned to the different grey levels the camera detects—the greater the light intensity, the brighter the color (white representing saturation of the CCD). Therefore, pH sensitivity can also be represented by a color change of each cone for the three pHs investigated.

Experiment 5: An Improved pH and Oxygen Concentration Sensor

An improved multiparameter fiber optic sensor was constructed that has both pH and pO$_2$ sensitive dye cones polymerized on its distal optic array surface. The two dye reagent admixture solutions used to make this dual parameter sensor are described below.

The pH sensing dye admixture was improved as follows. An aqueous solution of 5.67M acrylamide was prepared in phosphate buffer (pH 6.6). A solution of 0.0726M methylene bisacrylamide was prepared in n-propanol. A typical stock solution was comprised of 5 mls of acrylamide, 5 mls of bisacrylamide, 3.0 mgs of acryloyl fluorescein, preferably prepared in a glass container. The stock solution was then deoxygenated by bubbling molecular nitrogen into the prepared mixture for 20 minutes. In addition, a photoinitiator solution of 100 mgs of benzoin ethyl ether in 1 ml of n-propanol is freshly prepared. The final admixture is made by combining 1 ml of stock solution and 1 ml of the photoinitiator solution.

The oxygen sensing dye admixture was improved as follows. A stock solution was made by dissolving 20 mls of methylacryloxypropyl T-structure polydimethylsiloxane polymer [Petrarch Systems, Bristol, Pa.] in 20 mls of methylene chloride. An admixture was made by adding 100 mgs of tris 2,2'-bipyridyl ruthenium (II) chloride hexahydrate (Aldrich Company, Milwaukee, Wisc.] in 2 mls of n-propanol to 10 mls of the polymer solution. This admixture was then deoxygenated by bubbling molecular nitrogen in the solution for 15 minutes. In addition, a photoinitiator solution of 100 mgs of benzoin ethyl ether in 1 ml of methylene chloride is freshly prepared. The final admixture was prepared by adding 1 ml of the polymer/dye solution and 1 ml of the photoinitiator solution to a glass vial.

Figure 25A:
FIGS. 25A and 25B illustrate the capacity of a dual pH and $O_2$ sensor to detect oxygen in a sample.
Figure 25B:
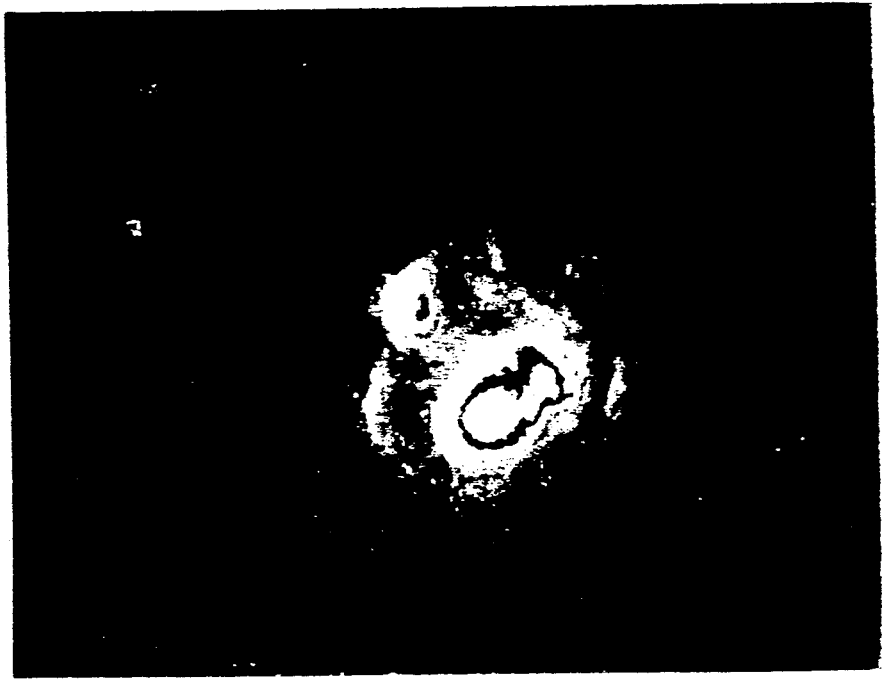

This dual pH and O$_2$ sensor was tested by submerging it in a pH 7.6 phosphate buffer solution saturated with molecular oxygen; or in a pH 7.6 phosphate buffer solution which has been deoxygenated. FIGS. 25A and 25B are video images of the distal face of the dual sensor. The smaller spot is the oxygen sensitive image and the large white spot is the pH sensitive image. The video image has been computer-processed to assign colors to the different intensity levels recorded by the camera. The images of FIGS. 25A and 25B show the response of the sensor to the oxygen saturated and deoxygenated buffers. Notice that the oxygen sensitive spot increases its intensity in the low oxygen buffer. This is consistent with the spectral properties of the ruthenium dye containing polymer. As the oxygen sensitive spot is exposed to higher concentrations of oxygen its fluorescence intensity decreases. It should be appreciated that as the concentration of oxygen changes, the fluorescence intensity of the ph-sensitive spot does not change.

Experiment 6: An Improved Sensor for Detection of pH and Carbon Dioxide Concentration A multiparameter sensor was constructed that has both pH and pCO$_2$ sensitive dye reagent cones polymerized on its distal face. The pH sensing dye cone was fabricated and deposited using the solution described in Experiment 5 previously. The pCO$_2$ dye sensing cone was prepared as follows:

The CO$_2$ sensing dye reagent is constructed of two regions: a pH island is laid down on the distal surface of the imaging fiber optic array using the same procedure as for depositing the pH dye, except the polymerization is monitored and stopped when the polymer island is still small, approximately 20 microns in height as appears from a side view. The distal surface is then soaked in 0.05M bicarbonate buffer. Second, a stock polymer solution is prepared by dissolving 5 mls of methylacryloxypropyl T-structure polydimethylsiloxane polymer [Petrarch Systems, Bristol, Pa.] in 5 mls of methylene chloride. In addition, a photoinitiator solution of 100 mgs of benzoin ethyl ether in 1 ml of methylene chloride is freshly prepared. The final dye admixture is prepared by adding 1 ml of the photoinitiator solution and 1 ml of the stock polymer solution to a glass vial.

Figure 26A:
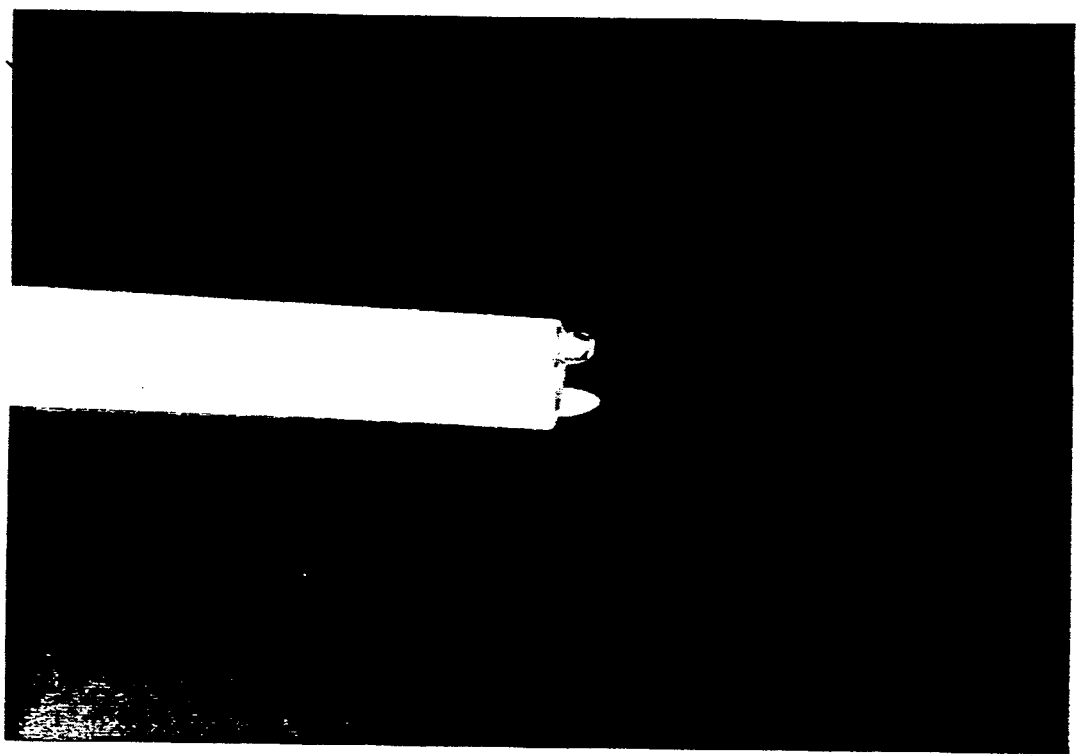
FIG. 26a-b is a photograph illustrating the construction of a $pCO_2$ sensing dye in a dual pH and $pCO_2$ sensor.
Figure 26B:
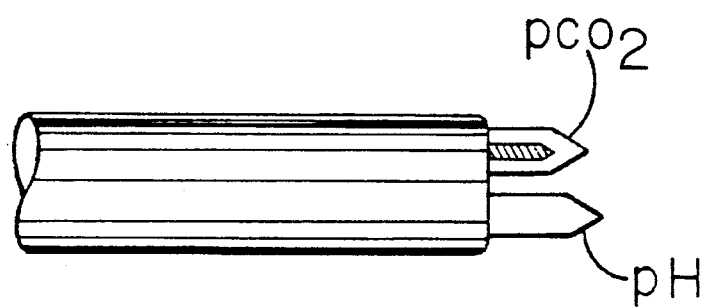

The pH and pCO$_2$ sensor is then prepared following the photopolymerization technique previously described herein. FIG. 26 shows the distal optic array surface of the fully constructed pH and pCO$_2$ sensor as a side view photographed under a light microscope. Clearly FIG. 26 reveals that the pCO$_2$ sensing dye cone is composed of two layers: a pH sensitive layer and a gas-permeable membrane. The pH layer appears as a small, white cone, whereas, the gas-permeable membrane is like a white halo covering the pH layer.

The present invention is not to be restricted in form nor limited in scope except by the claims appended hereto.

What we claim is:

1. A method for making a fiber optic sensor able to detect at least one analyte of interest in a fluid sample, said method comprising the steps of:

obtaining a preformed, unitary fluid optic array comprising a plurality of individually clad, fiber optic strands disposed co-axially along their lengths and having two discrete optic array ends each of which is formed of multiple strand end faces, said preformed, unitary fiber optic array being of determinable configuration and dimensions, said two discrete optic array ends of said preformed, unitary fiber optic array presenting two discrete optic array surfaces for introduction and conveyance of light energy;

preparing a photopolymerizable dye mixture comprising a light energy absorbing dye and a monomer mixture polymerizable by light energy;

placing one of said discrete optic array surfaces into contact with said photopolymerizable dye mixture;

introducing light energy to a first portion of the other discrete optic array surface of said preformed, unitary fiber optic array such that a first group of fiber optical strands within said preformed, unitary fiber optic array conveys and introduced light energy to a first spatial position on said contacted discrete optic array surface and causes said photopolymerizable dye mixture to photopolymerize at said first spatial position on said contacted discrete optic array surface as a first uninterrupted deposit of dye upon multiple strand end faces, said first spatially positioned uninterrupted deposit of dye reacting with one analyte of interest is a fluid sample; and introducing light energy to a second portion of the other discrete optic array surface of said preformed, unitary fiber optic array such that a second group of fiber optical strands within said preformed, unitary fiber optic array conveys said introduced light energy to a second spatial position on said contacted discrete optic array surface and causes said photopolymerizable dye mixture to photopolymerize at said second uninterrupted deposit of dye upon multiple strand end faces, said second spatially positioned uninterrupted deposit of dye reacting with one analyte of interest in a fluid sample.

2. A method for making a fiber optic sensor able to concurrently detect multiple analytes of interest in a fluid sample, said method comprising the steps of:

obtaining a preformed, unitary fiber optic array comprising a plurality of individually clad, fiber optic strands disposed co-axially along their lengths and having two discrete optic array ends each of which is formed of multiple strand end faces, said preformed, unitary fiber optic array being of determinable configuration and dimensions, said two discrete optic array ends of said preformed, unitary fiber optic array presenting two discrete optic array surfaces for introduction and conveyance of light energy;

preparing a first photopolymerizable dye mixture comprising a first light energy absorbing dye and a monomer mixture polymerizable by light energy;

preparing a second photopolymerizable dye mixture comprising a second light energy absorbing dye and a monomer mixture polymerizable by light energy;

placing one of said discrete optic array surfaces into contact with said first photopolymerizable dye mixture;

introducing light energy to a first portion of the other discrete optic array surface of said preformed, unitary fiber optic array such that a first group of fiber optical strands within said preformed, unitary fiber optic array conveys said introduced light energy to a first spatial position on said contacted discrete optic array surface and causes said first photopolymerizable dye mixture to photopolymerize at said first spatial position on said contacted discrete optic array surface as a first uninterrupted deposit of dye upon multiple strand end faces, said spatially positioned first uninterrupted deposit of dye reacting with one analyte of interest in a fluid sample;

placing said contacted discrete optic array surface of said preformed, unitary fiber optic array into additional contact with said second photopolymerizable dye mixture; and introducing light energy to a second portion of the other discrete optic array surface of said preformed, unitary fiber optic array such that a second group of fiber optical strands within said preformed, unitary fiber optic array conveys said introduced light energy to a second spatial position on said contacted discrete optic array surface and causes said second photopolymerizable dye mixture to photopolymerize at said second spatial position on said contacted discrete optic array surface as an second interrupted deposit of dye upon multiple strand end faces, said spatially positioned second uninterrupted deposit of dye reacting with one analyte of interest in a fluid sample.

3. The method for making a fiber optic sensor as recited in claim 1 or 2 wherein said light energy absorbing dye is selected from the group consisting of fluorophores, fluorescent enzyme substrates, and fluorescent antibody conjugates.

4. The method for making a fiber optic sensor as recited in claim 1 or 2 wherein said light energy absorbing dye is a chromophore.

5. The method for making a fiber optic sensor as recited in claim 1 or 2 wherein said photopolymerizable monomer mixture comprises acrylic acid derivatives.

6. The method for making a fiber optic sensor as recited in claim 1 or 2 wherein said light energy for photopolymerization is selected from the group consisting of infrared, visible and ultraviolet wavelengths.

* * * * *